United States Patent
Mangan et al.

(10) Patent No.: US 10,444,227 B2
(45) Date of Patent: Oct. 15, 2019

(54) NEURAL NETWORKS FORMED FROM CELLS DERIVED FROM PLURIPOTENT STEM CELLS

(71) Applicant: FUJIFILM Cellular Dynamics, Inc., Madison, WI (US)

(72) Inventors: Kile P. Mangan, Madison, WI (US); Coby B. Carlson, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 0 days.

(21) Appl. No.: 14/830,162

(22) Filed: Aug. 19, 2015

(65) Prior Publication Data

US 2016/0116459 A1    Apr. 28, 2016

Related U.S. Application Data

(60) Provisional application No. 62/039,244, filed on Aug. 19, 2014.

(51) Int. Cl.
| | | |
|---|---|---|
| *A61K 31/00* | (2006.01) | |
| *G01N 33/50* | (2006.01) | |
| *C12N 5/0793* | (2010.01) | |
| *G01N 33/483* | (2006.01) | |

(52) U.S. Cl.
CPC ....... *G01N 33/5058* (2013.01); *C12N 5/0619* (2013.01); *G01N 33/4836* (2013.01); *C12N 2502/081* (2013.01); *C12N 2503/00* (2013.01); *C12N 2506/45* (2013.01); *C12N 2531/00* (2013.01)

(58) Field of Classification Search
CPC .................... G12N 5/0619; G01N 33/5058
See application file for complete search history.

(56) References Cited

U.S. PATENT DOCUMENTS

| | | |
|---|---|---|
| 7,820,439 B2 | 10/2010 | Alam et al. |
| 8,153,428 B2 | 4/2012 | Carpenter et al. |
| 8,252,586 B2 | 8/2012 | Carpenter et al. |
| 8,426,200 B2 | 4/2013 | Verfaillie et al. |
| 8,513,017 B2 | 8/2013 | Sugaya et al. |
| 8,546,140 B2 | 10/2013 | Mack et al. |
| 8,735,149 B2 | 5/2014 | Reubinoff et al. |
| 8,741,648 B2 | 6/2014 | Rajesh et al. |
| 8,796,022 B2 | 8/2014 | Bissonnette et al. |
| 2002/0168766 A1 | 11/2002 | Gold et al. |
| 2003/0022367 A1 | 1/2003 | Xu |
| 2003/0211603 A1 | 11/2003 | Earp et al. |
| 2007/0238170 A1 | 10/2007 | Thomson et al. |
| 2008/0171385 A1 | 7/2008 | Bergendahl et al. |
| 2009/0029462 A1 | 1/2009 | Beardsley et al. |
| 2011/0104125 A1 | 5/2011 | Yu |
| 2012/0276063 A1 | 11/2012 | Meyer et al. |
| 2015/0265652 A1 | 9/2015 | George et al. |

FOREIGN PATENT DOCUMENTS

| | | |
|---|---|---|
| WO | WO 2004/051560 | 6/2004 |
| WO | WO 2005/021704 | 3/2005 |
| WO | WO 2010/042669 | 4/2010 |
| WO | WO 2011/091048 | 7/2011 |
| WO | WO 2011/130675 | 10/2011 |
| WO | WO 2012/019122 | 2/2012 |
| WO | WO 2012/080248 | 6/2012 |
| WO | WO 2013/067362 | 5/2013 |
| WO | WO 2013/163228 | 10/2013 |
| WO | WO 2014/172580 | 10/2014 |

OTHER PUBLICATIONS

Hussain (Science, 307 (5713), 1207-1208, 2005).*
Sohya et al (The Journal of Neuroscience, 27(8): 2145-2149, 2007).*
Izhikevich (IEEE Transactions on Neural Networks, 15(5): 1063-1070, 2004).*
Soussou et al, (IEEE Transactions on Biomedical Engineering, 54(7): 1309-1320, 2007) (Year: 2007).*
Xue et al (Nature, 511: 596-600, 2014, Epub Jun. 22, 2014) (Year: 2014).*
LaFee (PDF, The Brain's Balancing act, Editorial, Jun. 22, 2014). (Year: 2014).*
"Measuring neuronal activity: extracellular single-unit recordings on the maestro multielectrode array," iCell® Neurons Application Protocol, Cellular Dynamics International, pp. 1-8, May 2014.
Allen et al. "Astrocyte glypicans 4 and 6 promote formation of excitatory synapses via GluA1 AMPA receptors," *Nature*, 486:410-414, 2012.
Bailey et al., "In vitro CNS tissue analogues formed by self-organisation of reaggregated post-natal brain tissue," *Journal of Neurochemistry*, 117(6):1020-1032, 2011.
Bandy et al., "Neuronal human neurons in medium that supports basic synaptic functions and activity of vitro," *Proc Natl Acad Sci U S A*, 112(20):E2725-E2734, 2015.
Chen et al., "Integration of external signaling pathways with the core transcriptional network in embryonic stem cells," *Cell*, 133:1106-1117, 2008.
Chen et al., "Chemically defined conditions for human iPSC derivation and culture," *Nature Methods*, 8:424-429, 2011.
Dani et al., "Reduced cortical activity due to a shift in the balance between excitation and inhibition in a mouse model of Rett syndrome," *Proc. Natl. Acad Sci U S A*, 102(35):12560-12565, 2005.
Gibson et al., "Imbalance of neocortical excitation and inhibition and altered UP states reflect network hyperexcitability in the mouse model of fragile X syndrome," *J. Neurophysiol*, 100:2615-2626, 2008.
Hagerman and Hagerman, "The fragile X premutation: into the phenotypic fold," *Curr. Opin. Genet. Dev.*, 12:278-283, 2002.
Hogberg et al., "Application of micro-electrode arrays (MEAs) as an emerging technology for developmental neurotoxicity: evaluation of domoic acid-induced effects in primary cultures of rat cortical neurons," *NeuroToxicology*, 32(1):158-168, 2011.

(Continued)

*Primary Examiner* — Anoop K Singh
*Assistant Examiner* — Magdalene K Sgagias
(74) *Attorney, Agent, or Firm* — Parker Highlander PLLC

(57) ABSTRACT

In some aspects, cultures of neurons derived from human induced pluripotent stem cells (iPS cells) that exhibit synchronous firing of neural networks are provided. In some embodiments, neuronal activity of the cultures may be detected or measured using a multi-electrode array.

22 Claims, 16 Drawing Sheets

(56) References Cited

OTHER PUBLICATIONS

Johnstone et al., "Microelectrode arrays: a physiologically based neurotoxicity testing platform for the 21$^{st}$ century," *NeuroToxicology*, 31(4):331-350, 2010.
Ludwig et al., "Derivation of human embryonic stem cells in defined conditions," *Nat. Biotechnol.*, 24(2):185-187, 2006.
Ludwig et al., "Feeder-independent culture of human embryonic stem cells," *Nat. Methods*, 3(8):637-646, 2006.
Mangan et al., "Measuring pharmaco-influences on neural networks," *Genetic Engineering and Biotechnology News*, 34(9):1-2, 2014.
Massimini et al., "Cortical mechanisms of loss of consciousness: insight from TMS/EEG studies", *Arch Ital Biol*, 150(2-3):44-55, 2012.
McConnell et al., "Evaluation of multi-well microelectrode arrays for neurotoxicity screening using a chemical training set," *NeuroToxicology*, 33(5):1048-1057, 2012.
PCT International Search Report and Written Opinion issued in International Application No. PCT/US2015/045869, dated Oct. 26, 2015.
Schwartz et al., "Differentiation of neural lineage cells from human pluripotent stem cells," *Methods*, 45(2):142-158, 2008.
Tabuchi et al., "A neuroligin-3 mutation implicated in autism increases inhibitory synaptic transmission in mice," *Science*, 318:71-76, 2007.
Takahashi and Yamanaka, "Induction of pluripotent stem cells from mouse embryonic and adult fiberoblast cultures by defined factors," *Cell*, 126:663-676, 2006.
Takahashi et al., "Induction of pluripotent stem cells from adult human fibroblasts by defined factors," *Cell*, 131:861-872, 2007.
Van Vliet et al., "Electrophysiological recording of re-aggregating brain cell cultures on multi-electrode arrays to detect acute neurotoxic effects," *NeuroToxicology*, 28(6):1136-1146, 2007.
Wainger et al., "Intrinsic membrane hyperexcitability of amyotrophic lateral sclerosis patient-derived motor neurons," *Cell Reports*, 7(1):1-11, 2014.
Yu and Thomson, "Pluripotent stem cell lines," *Genes Dev.*, 22(15):1987-1997, 2008.
Yu et al., "Induced pluripotent stem cell lines derived from human somatic cells," *Science*, 318:1917-1920, 2007.
Yu et al., "Human induced pluripotent stem cells free of vector and transgene sequences," *Science*, 324(5928):797-801, 2009.
Zhang and Sun, "The balance between excitation and inhibition and functional sensory processing in the somatosensory cortex," *Int Rev Neurobiol*, 97:305-33, 2011.
Zhang et al., "Rapid single-step induction of functional neurons from human pluripotent stem cells," *Neuron*, 78:785-798, 2013.
Shi et al., "Human cerebral cortex development from pluripotent stem cells to functional excitatory synapses," *Nat Neurosci.*, 15(3):477-486, 2012.
Li et al., "Long-term recording on multi-electrode array reveals degraded inhibitory connection in neuronal network development," *Biosensors and Bioelectronics*, 22:1538-1543, 2007.
Office Action issued in European Application No. 15757376.7, dated Dec. 11, 2017.
Office Action issued in European Application No. 15757376.7, dated Sep. 12, 2018.
Response filed in European Application No. 15757376.7, dated Jan. 21, 2019.
Ito et al., "Developmental process and synchronized bursts in cultured neuronal networks," *Seibutsu Butsuri*, 54(4):210-214, 2014.
Office Action issued in Japanese Application No. 2017-509656, dated Apr. 2, 2019.
Liu, Yan, et al. "Directed differentiation of forebrain GABA interneurons from human pluripotent stem cells." Nature protocols 8.9 (2013): 1670-1679.†
Shi, Yichen, Peter Kirwan, and Frederick J. Livesey. "Directed differentiation of human pluripotent stem cells to cerebral cortex neurons and neural networks." Nature protocols 7.10 (2012): 1836-1846.†
Aigner, Stefan, et al. "Human pluripotent stem cell models of autism spectrum disorder: emerging frontiers, opportunities, and challenges towards neuronal networks in a dish." Psychopharmacology 231.6 (2014): 1089-1104.†

\* cited by examiner
† cited by third party

NEURAL NETWORKS FORMED FROM CELLS DERIVED FROM PLURIPOTENT STEM CELLS

This application claims the benefit of U.S. Provisional Patent Application No. 62/039,244, filed Aug. 19, 2014, the entirety of which is incorporated herein by reference

BACKGROUND OF THE INVENTION

1. Field of the Invention

The present invention relates generally to the field of molecular biology, cell biology, and medicine. More particularly, it concerns mixing or combining cultures of neurons derived from pluripotent stem cells and methods of using such mixed cell cultures.

2. Description of Related Art

The mammalian brain works appropriately only when there is a proper balance between excitation and inhibition. An imbalance in the excitatory-inhibitory (E/I) ratio is associated with abnormal sensory processing and unconsciousness (Zhang and Sun, 2011; Massimini et al., 2012). Increased E/I ratios can lead to prolonged neocortical circuit activity, stimulus hypersensitivity, cognitive impairments and epilepsy (Hagerman and Hagerman, 2002; Gibson et al., 2008: reviewed in Zhang and Sun, 2011). Similarly, decreases in the E/I ratio have been linked to abnormalities such as impaired social interaction and autistic behaviors, and mental retardation (Rett Syndrome) (Tabuchi et al., 2007; Dani et al., 2005; reviewed in Zhang and Sun, 2011). It has been well studied and determined that the E/I ratio changes during development, with excitation decreasing and inhibition increasing, and that deviations in these changes for either can disrupt the E/I ratio (reviewed in Zhang and Sun, 2011). With the dramatic rise in the incidence of neurological diseases, there is a need for improved therapies. However, access to clinically-relevant cell models continues to be a major challenge in neuroscience research and drug development. Human induced pluripotent stem cell (iPSC)-derived neurons provide a cell type that may be used to facilitate an improved understanding of the mechanisms of neurological diseases. Clearly, there is a need for in vitro approaches that can more effectively simulate in vivo systems.

SUMMARY OF THE INVENTION

The present invention overcomes limitations in the prior art by providing, in some aspects, improved cultures of neurons derived from induced pluripotent stem cells (iPSC or iPS cells) that can display synchronous bursting of neural networks in vitro. In some aspects, ratios of excitatory neurons and inhibitory neurons are co-cultured, optionally with additional astrocytes. These cultures of neurons may be used, e.g., to detect changes in network communication resulting from exposing the neural culture to a test compound. In some embodiments, synchronous neural networks are generated by mixing excitatory and inhibitory neurons and then measuring spontaneous synchronous neural bursting using a multi-electrode array.

An aspect of the present invention relates to an in vitro method for producing a population of neurons, comprising: (a) combining a plurality of excitatory neurons and inhibitory neurons in vitro, and (b) culturing the neurons for a period of time sufficient to allow for the formation of a neural network; wherein both the excitatory neurons and the inhibitory neurons are derived from pluripotent stem cells; and wherein the ratio of excitatory neurons to inhibitory neurons is sufficient to allow for the generation of synchronous neuron firing or synchronous action potentials. The culture of neurons may further comprise astrocytes, wherein the astrocytes are derived from pluripotent stem cells. The pluripotent stem cells may be human induced pluripotent stem (iPS) cells. The pluripotent stem cells may be iPS cells derived from a mouse, rat, primate, ape, or monkey. In some embodiments, the iPS cells are derived from a healthy donor (e.g., a healthy human donor). In some embodiments, the iPS cells are derived from a subject with a disease (e.g., a human with a disease, such as a genetic disease). The disease may be a neurological or neurodegenerative disease. The disease may be, e.g., autism, epilepsy, schizophrenia, ADHD, ALS, or a bipolar disorder. The population of neurons may comprise from about 30% to about 90% excitatory neurons and from about 10% to about 70% inhibitory neurons. The population may comprise about 30, 35, 40, 45, 50, 55, 60, 65, 70, 75, 80, 85, or 90% excitatory neurons, or any range derivable therein. The population may comprise about 10, 15, 20, 25, 30, 35, 40, 45, 50, 55, 60, 65, or 70% inhibitory neurons, or any range derivable therein. The population of neurons may be cultured, incubated, and/or provided in a solution or a media having an osmolarity of about 300-320, about 305-315, or about 300, 305, 310, 315, 320 mOsmol, or any range derivable therein. The solution or media may be supplemented with 1, 2, 3, 4, 5, or more or all of: N2, B27, retinoic acid, brain-derived neurotrophic factor (BDNF), glia cell-derived neurotrophic factor (GDNF), ascorbic acid, cAMP, laminin, and/or cholesterol. In some embodiments, the population of neurons further comprises from about 5% to about 25% astrocytes, wherein the astrocytes are derived from iPS cells (iPSC) such as, e.g., human iPS cells. The astrocytes may be derived from human iPS cells; for example, the astrocytes can be derived from human iPS cells, wherein the iPS cells were produced from cells from a healthy donor or a diseased donor. In some embodiments, the population of neurons comprises a mixture of a first culture of excitatory neurons derived from pluripotent stem cells and a second culture of inhibitory neurons derived from pluripotent stem cells; wherein the first culture comprises at least about 70% GABAergic neurons; and wherein the second culture comprises at least about 90% glutamatergic neurons. In some embodiments, the pluripotent stem cells are human induced pluripotent stem (iPS) cells. The population may comprises from about 90% to about 20% of the first culture and from about 10% to about 80% of the second culture. The population of neurons may further comprise from about 5% to about 25% astrocytes, wherein the astrocytes are derived from iPSC. In some embodiments, the population of neurons is cultured on a multi-electrode array (e.g., a Maestro MEA, an Axion MEA; Axion Biosystems, Atlanta, GA). The multi-electrode array may comprise at least 8 electrodes. In some embodiments, the multi-electrode array comprises at least 16 electrodes. For example, the multi-electrode array may contain at least 8, at least 16, at least 32, or at least 64 electrodes within each well in the multi-electrode array. In some embodiments, within each well of the multi-electrode array, at least 8, 16, 32, or 64 individual embedded microelectrodes (e.g., about 30-50 μm diameter; about 200-350 μm center-to-center spacing; optionally with integrated Ground electrodes) may be used to simultaneously monitor the activity of the neurons. The multi-electrode array may comprise a plurality of cultures of said neurons in distinct wells in the multi-electrode array, wherein the ratios of excitatory to inhibitory neurons varies between the cultures. In some embodiments, the excitatory neurons are glutamatergic, dopaminergic, or cholinergic neurons. In some embodiments, the inhibitory neurons are GABAergic neurons. The population of neurons may comprise cortical neurons, dopaminergic neurons, cholinergic neurons, hippocampal neurons, amygdala neurons, peripheral neurons, motor neurons, or neurons expressing nociceptors. The method may further comprise contacting the population of neurons with a test compound. In some embodiments, the test compound can modulate neurotransmission. In some embodiments, the method further comprises detecting or measuring the electrical or neuronal activity of the population. In some embodiments, said detecting or measuring comprises measuring the voltage produced by said population. Data from said detecting or measuring may be analyzed, e.g., using the iCell® NeuroAnalyzer.

Another aspect of the present invention relates to a culture of neurons as described herein or as produced by a method of the present invention. The culture may comprise excitatory neurons, inhibitory neurons, and a neural network, wherein the ratio of excitatory neurons to inhibitory neurons is sufficient to allow for the generation of synchronous neuron firing or synchronous action potentials. In some embodiments, the neurons are comprised in or on a multi-electrode array.

Yet another aspect of the present invention relates to a culture of neurons comprising a plurality of excitatory neurons and inhibitory neurons wherein both the excitatory neurons and the inhibitory neurons are derived from pluripotent stem cells; and wherein the ratio of excitatory neurons to inhibitory neurons is sufficient to allow for the generation of synchronous neuron firing or synchronous action potentials. As described herein, the pluripotent cells may be induced pluripotent cells, e.g., from a healthy or diseased mammalian or human subject, as described herein. The culture of neurons may be provided on a multi-electrode array, e.g., as described herein. The ratio of excitatory to inhibitory neurons may or may not be varied in different wells of the multi-electrode array. The population of neurons may be cultured, incubated, and/or provided in a solution or media (e.g., a physiologically acceptable cell media) having an osmolarity of about 300-320, about 305-315, or about 300, 305, 310, 315, 320 mOsmol, or any range derivable therein. The neuron culture in each well of the multi-electrode array may be incubated in or comprise in each well a media as described herein such as, e.g., a media as described in Bardy et al., 2015 or WO2014172580. The media may be supplemented with 1, 2, 3, 4, 5, or more or all of: N2, B27, retinoic acid, brain-derived neurotrophic factor (BDNF), glia cell-derived neurotrophic factor (GDNF), ascorbic acid, cAMP, laminin, and/or cholesterol. The culture of neurons may comprise astrocytes. In some embodiments, one or more of the neural cells is transgenic or genetically altered. In some embodiments, the culture of neurons further comprises a plurality of induced pluripotent stem cells and/or neural precursor cells, e.g., present with the neural cells in a multi-electrode array, as described herein.

As used herein, an "excitatory neuron" refers to a neuron that, when it releases neurotransmitter (e.g., glutamate) at a synaptic cleft as the presynaptic neuron, increases the probability of an action potential in the postsynaptic neuron. As used herein, an "inhibitory neuron" refers to a neuron that, when it releases neurotransmitter (e.g., gamma-aminobutyric acid (GABA)) at a synaptic cleft as the presynaptic neuron, decreases the probability of an action potential in the postsynaptic neuron.

As used herein, "synchronous neuronal firing", "synchronous neuron firing", and "synchronous action potentials" are used interchangeably herein and refer to a repeated firing of neurons over a period of time, e.g., to generate a neural oscillation or a repeated burst of neuronal action potentials. The neural oscillations may be characterized by their frequency, amplitude, and phase. As would be appreciated by one of skill in the art, synchronous neural firing or synchronous action potentials can be detected by a variety of electrophysiological techniques.

In some aspects, a mixture of neural cells is provided wherein the cells are derived from pluripotent stem cells such as, e.g., human iPS cells. The mixture may comprise a combination of excitatory and inhibitory neurons that are classified as, e.g., cortical neurons, dopaminergic neurons, cholinergic neurons, hippocampal neurons, amygdala neurons, peripheral neurons, motor neurons, and/or neurons expressing nociceptors. The mixture of excitatory and inhibitory neural cells may be found in the same general neuroanatomical region of the brain or in different neuroanatomical regions of the brain in vivo (e.g., in the brain of a mammalian subject such as a human, a primate, an ape, a monkey, a mouse, or a rat, etc.).

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 9: top) are shown Cultures grown in Brain Phys (BP) medium both resulted in increased mean firing rates (upper: red) and synchrony (upper: purple), as compared to control (maintenance medium: MM), and also produced a more stabilized neural network (* all comparison's p<0.05). Notably, BP shifted the culture network's activity from high-frequency, short channel (Poisson-captured) bursting behaviors (box: left) seen in MM to high-frequency, long-lasting network (ISI-captured) bursting behaviors (box: right) that incorporate a larger percentage (%) of channel-bursting activity (bottom).

DESCRIPTION OF ILLUSTRATIVE EMBODIMENTS

Figure 1:
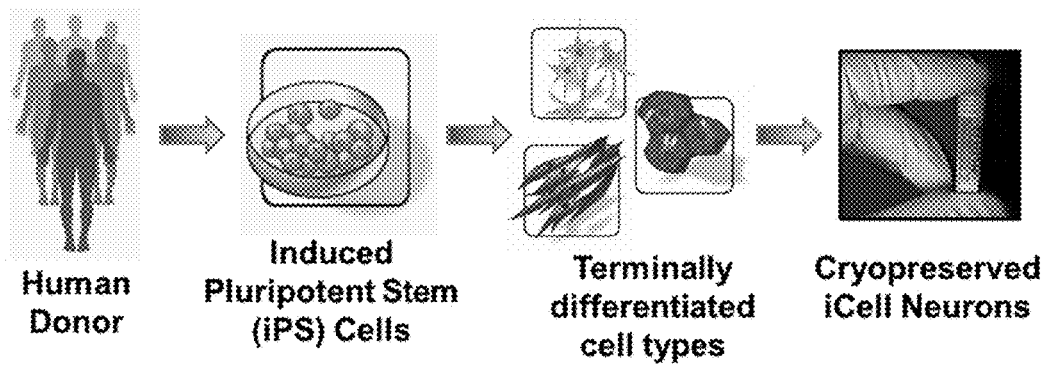
FIG. 1: Schematic for the generation of cryopreserved iCell® Neurons.

The present invention is based, in part, on the discovery that combinations of excitatory and inhibitory neurons can be mixed or combined in vitro to form neural networks that can display synchronous firing. In some embodiments, it has been found that particular ratios of excitatory neurons to inhibitory neurons (E/I ratio) can be effectively utilized to form the neural networks. The E/I ratio within a neuronal cell culture may be generated by combining different cell-types (e.g., iCell® Neurons, iCell® DopaNeurons, Glutamatergic X, where X equals the percent of glutamateric neurons) that are derived from pluripotent stem cells such as human iPS cells. For example, one, two, three, or more cultures of neurons that vary in the E/I ratio may be produced from human iPS cells and combined and cultured in vitro to produce a neural network. The iPS cells may, in various embodiments, be derived from a healthy patient or a patient with a disease such as a neurological or neurodegenerative disease. As shown in the below examples, the Axion Maestro multi-electrode array (MEA) platform was used to assess the neuronal activity, synchrony, and bursting behaviors in iPS cell-derived neuronal cultures of various E/I ratios. In some embodiments, astrocytes derived from pluripotent stem cells such as human iPS cells (e.g., iCell® Astrocytes) may also be added to the cultures. Analysis may be performed, e.g., via the Neural Metrics statistics toolbox (Axion). As shown in the below examples, the results support the idea that the E/I ratio can be used to modulate neuronal-network synchronicity, expansion, and proclivity for seizures. The cultures and methods provided herein may be particularly useful, e.g., for toxicity screening and/or the screening or testing of compounds that may be therapeutically useful for modulating neurotransmission.

I. Generation of Synchronous Networks from Ratios of Different Cell Types

In some embodiments, ratios of different cells can be combined in vitro to produce synchronous networks of neurons. For example, in some embodiments, ratios of excitatory and inhibitory neurons may be combined in vitro (e.g., in a multi-well plate such as a multi-electrode array) to produce neural networks that exhibit synchronous firing that may be recorded, e.g., via electrophysiological techniques. In some embodiments, the neuron cultures do not include astrocytes. Nonetheless, in some embodiments, astrocytes may be included in combination with excitatory and/or inhibitory neurons in vitro.

Depending upon the intended use of the neural networks formed, different ratios of excitatory verses inhibitory neurons may be used to produce the neuronal or neural networks. For example, if in vitro recapitulation of a neural disease phenotype characterized by increased activity of excitatory neurons or decreased activity of inhibitory neurons is desired (e.g., epilepsy), then a higher proportion of excitatory neurons compared to inhibitory neurons may be used, e.g., with E:I ratios of about 100:0, 90:10, 80:20, or 70:30, or any range derivable therein. Alternatively, if in vitro recapitulation of a neural disease phenotype associated with decreased activity of excitatory neurons or increased activity of inhibitory neurons is desired (e.g., an autism spectrum disorder), then a neural culture having a range of proportions of inhibitory neurons compared to excitatory neurons may be used, e.g., with E:I ratios of about 20:80, 25:75, 30:70, 35:65, 40:60, or any range derivable therein. For example, a culture having an E:I ratio of about 0:100, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 100:0, or any range derivable therein, may be used. In some embodiments, if in vitro recapitulation of a non-diseased phenotype is desired, then an approximate equal number of excitatory neurons compared to inhibitory neurons may be used, or preferably with a ratio of E to I approximately 80:20, 75:25, 70:30, 60:40, 55:45, 50:50, or any range derivable therein including all combinations therein.

The neural culture or neural network may further comprise astrocytes. In some embodiments, astrocytes may comprise about 1, 2.5, 5, 10, 15, 20, 25, 35, 40, 45, 50, or 55%, or any range derivable therein, of the neural culture or neural network. In some embodiments, at least about 1 k (i.e., about 1000), 2.5 k, 5 k, 10 k, 15 k, 20 k, 25 k, or more astrocytes may be added to a culture comprising excitatory and inhibitory neurons.

A variety of cell populations derived from pluripotent stem cells such as human induced pluripotent stem cells (iPSC) may be used in various embodiments of the instant application; these cell population types include, e.g., cortical (GABAergic/inhibitory) neurons, dopaminergic neurons, cholinergic neurons, serotoninergic neurons, glutamatergic neurons, neurons that express strychnine-sensitive glycine receptors, acetylcholine neurons, epinephrine or norepinephrine neurons, histamine responsive neurons, an A delta or C group pain fiber, neurons expressing nociceptors, and astrocytes. In some embodiments, neuronal types typically found in the hippocampus, amygdala, periphery (peripheral neurons), motor neurons, or cortical neurons (e.g., glutamatergic or excitatory neurons) may be used in various embodiments. For example, in some embodiments, cholinergic neurons may be generated as described, e.g., in U.S. Pat. Nos. 8,513,017 or 8,796,022. In some embodiments, motor neurons may be generated as described, e.g., in U.S. Pat. No. 8,735,149. In some embodiments, dopaminergic neurons may be generated as described in WO2013067362; WO2013163228; WO2012080248; or WO2011130675.

A variety of methods may be used to generate and maintain induced pluripotent stem cells (iPSC or iPS cells). For example iPS cells may be generated as described in Yu et al. (2007), Yu et al. (2008), Yu et al. (2009), Takahashi et al., (2006), Takahashi et al. (2007), U.S. Pat. Nos. 8,546,140, 8,741,648 or U.S. Pat. Publication 2011/0104125. iPS cells may be cultured and maintained in an undifferentiated state, e.g., using methods as described in U.S. Pat. Publication 2007/0238170, U.S. Pat. Publication 2003/0211603, and U.S. Pat. Publication 2008/0171385, and/or U.S. Pat. Publication 2009/0029462. In certain embodiments, undefined conditions may be used; for example, pluripotent cells may be cultured on fibroblast feeder cells or a medium that has been exposed to fibroblast feeder cells in order to maintain the stem cells in an undifferentiated state. Alternately, pluripotent cells may be cultured and maintained in an essentially undifferentiated state using defined, feeder-independent culture system, such as a TeSR medium (Ludwig et al., 2006a; Ludwig et al., 2006b) or E8 or Essential8 medium (Chen et al., 2011: PCT/US2011/046796).

In some embodiments, specific ratios of excitatory to inhibitory neurons may be seeded into a single well or container in vitro in order to generate a neural network that produces synchronous neural firing in vitro. In some embodiments, the following ratios of excitatory (e.g., glutamatergic) neurons to inhibitory neurons (e.g., GABAergic neurons), are seeded or cultured at E:I ratios of about 90:10, 85:15, 80:20, 75:25, 70:30, 65:35, 60:40, 55:45, 50:50, or any range derivable therein, e.g., to produce neural networks or cultures that can display synchronous neural firing in vitro.

II. Methods for Culturing Neurons In Vitro

In some embodiments, neurons are cultured in vitro to allow for the formation of neural networks. The neurons may optionally be cultured or co-cultured with astrocytes. In some embodiments, the neurons are cultured on a multiwell plate such or a multiwell electrode array. For example, the Axion BioSystems multielectrode array (MEA) is an example of a multiwell electrode array that may be used in some embodiments. The MEA system includes electrodes in each well that may be used for detection of neuronal electrical activity, and MEA plates may have 48 or 96 wells. Multichannel Systems (Reutlingen, Germany) and NeuroNexus (Ann Arbor, MI) also produce commercially available multi-electrode arrays that may be used in various embodiments of the present invention. Nonetheless, in some embodiments, cells may be cultured in a culture dish or multiwell dish and then separately measured using another technique to detect neural activity of cells; for example, other eletrophysiological techniques that may be to detect synchronous firing of neurons include, e.g., FLIPR calcium assessing and voltage-sensitive dyes and/or proteins (VIPs). Generally, it is envisioned that essentially any technique that involves measuring or detecting the network bursting, network level communication, network connectivity, neural conductivity, connectivity, or synchronous neuron bursting or firing may be used with the present invention.

In some embodiments, the Axion BioSystems' Maestro multielectrode array (MEA) technology is used. The MEA allows for a non-invasive, label-free platform that can be used to measure the electrical activity of single cells or a cellular network. In some embodiments, neurons derived from IPS cells (e.g., iCell® Neurons, iCell® DopaNeurons) can be thawed and cultured directly on MEAs to form neuronal networks amenable to electrophysiological interrogation. iCell® NeuroAnalyzer, a MATLAB-based script, and/or Axion's Neural Metrics may be used to analyze the neuronal electrical activity detected on the Maestro MEA system. Together, these approaches may be used as a non-invasive platform for assessing the potential effects of compound modulation of neurotransmission.

A variety of media may be used to culture the neurons in vitro. In some embodiments, Artificial Cerebro-Spinal Fluid (ACSF) may be used to culture neurons in vitro. Generally, the media may have an appropriate inorganic salt concentration (e.g., similar to DMEM/F12 media), an appropriate osmolarity (e.g., about 305-315 mOsmol), and a pH equal to about 7.4. In some embodiments, BrainPhys media (The Salk Institute, La Jolla, Calif.; Bardy et al., 2015; WO2014172580) may be used to culture cells. BrainPhys media may optionally be supplemented with N2, B27, retinoic acid, brain-derived neurotrophic factor (BDNF), glia cell-derived neurotrophic factor (GDNF), ascorbic acid, cAMP, laminin, and cholesterol, e.g., to promote further differentiation of undifferentiated cells or neural precursor cells in the culture. In some embodiments, the media used allows for spontaneous and evoked action potentials, network spontaneous calcium activity, excitatory synaptic activity, and a glucose level that is comparable to physiological conditions. In some embodiments, the media may include neurotransmitters (e.g., GABA, glutamate, acetylcholine, and/or dopamine), glypican 4, and/or glypican 6, as desired to promote spontaneous neurotransmission. In other embodiments, the media added to a neural culture has no or only trace amounts of neurotransmitters.

It is envisioned that a regular aCSF-type medium or a regular aCSF-type medium may further comprise an astrocyte factor in order to promote excitatory synaptic formation (e.g., glypican 4 and/or glypican 6; Allen et al., 2010). In some embodiments, it is envisioned that the following aCSF media may be used: aCSF (low Mg+): 125 mM NaCl, 25 mM NaHCO$_3$, 2.5 mM KCl, 1.25 mM NaH$_2$PO$_4$, 2.8 mM CaCl$_2$, 0.2 mM MgCl$_2$, 25 mM D-Glucose, 13.87 M sucrose, bubbled with 95% O$_2$ and 5% CO$_2$. The medium may be about pH 7.4. The aCSF-type medium may further comprise about 4-10 nM or 8 nM glypican 4 and/or about 4-10 nM or 8 nM glypican 6. In some embodiments, the media has been modified to reduce or eliminate levels of neuroactive amino acids (glutamate, aspartate, glycine alanine, serine) that could affect glutamatergic or GABAergic synaptic activity. The medium may comprise a NaCl concentration that is similar to neurophysiological levels, e.g., about 120-125 nM. The medium may contain calcium levels similar to those in human cerebrospinal fluid in vivo, e.g., a Ca$^{2+}$ of about 1.1 mM. The media may have an osmolarity of about 300-315, 300-305, 300-310, 300, 305, 310, 315 mOsmol, from greater than about 300 to about 315 mOsmol, or any range derivable therein.

III. Methods for Producing Neurons and Astrocytes from Pluripotent Cells

A variety of methods are available for generating neurons and/or astrocytes for use in various aspects of the present invention. In some embodiments, neurons (e.g., GABAergic, glutamatergic, or dopaminergic neurons, etc.) or astrocytes may be cultured produced from pluripotent cells such as iPS cells or stem cells. In some embodiments, neurons may be differentiated prior to culture in a well comprising a multielectrode array (e.g., a MEA); in other embodiments, cells that are undifferentiated, pluripotent, multipotent, or neural progenitor cells may be placed in a well comprising a multielectrode array and then differentiated into neural cells.

In some embodiments, the neurons or astrocytes are generated from iPS cells that were generated from cells obtained from a healthy donor. In other embodiments, the donor has a disease. For example, in some embodiments the donor has a disease such as a neurological or neurodegenerative disease such as, e.g., epilepsy, autism, attention deficit-hyperactivity disorder (ADHD), amyotrophic lateral sclerosis (ALS), Charcot-Marie-Tooth (CMT), Huntington's disease, familial epilepsy, schizophrenia, familial Alzheimer's disease, Friedreich ataxia, spinocerebellar ataxia, spinal muscular atrophy, hereditary spastic paraparesis, leukodystrophies, phenylketonuria, Tay-Sachs disease, Wilson disease, an addiction disorder, depression, or a mood disorder. The disease may be a genetic disease or an increased genetic susceptibility to a particular neurological disease.

In some embodiments, the following methods may be used to generate GABAergic, glutamatergic, dopaminergic, or cholinergic neurons from pluripotent stem cells such as embryonic stem cells or iPS cells. For example, in some embodiments, the methods of U.S. Patent Application 2012/0276063 may be used to generate neurons from pluripotent stem cells. For example, in some embodiments, bFGF and TGFβ may be excluded from a media (e.g., excluded from a defined media such as TeSR or Essential8 media) that is used to culture pluripotent cells such as iPS cells prior to the start of aggregate formation (while cells were still in adherent culture), then this may be used to promote neuronal differentiation of the pluripotent cells. In some embodiments, when iPS cells are "primed" in the absence of TeSR growth factors, i.e., cultured in any medium that does not have basic fibroblast growth factor (bFGF) and transforming growth factor β (TGFβ), for several days prior to aggregate formation, the cells can develop into the neural lineage with purity, rapidity and consistency. Other methods for making neurons include Zhang et al. (2013), U.S. Pat. No. 7,820,439, PCT Publn. No. WO 2011/091048, U.S. Pat. Nos. 8,153,428, 8,252,586, and 8,426,200.

A variety of methods may be used to generate astrocytes from pluripotent stem cells such as embryonic stem cells or iPS cells. These methods include, e.g., U.S. Patent Application 2012/0276063, which are incorporated by reference herein in their entirety without disclaimer.

In some embodiments, the method of Studer et al. may be used to generate dopaminergic neuronal cells (PCT Publn. No. WO2013/067362, incorporated herein by reference). These results showed that dopaminergic neurons produced via this method can be efficiently engrafted in vivo. In some embodiments, the method described in U.S. patent application Ser. No. 14/664,245 may be used to generate dopaminergic neuronal cells.

Cultures of neuronal cell types that are derived from pluripotent cells, including iPS cells, are also commercially available and may be purchased. For example, iCell® Neurons, iCell® DopaNeurons, and iCell® Astrocytes are derived from human iPS cells and may be purchased from Cellular Dynamics International (Madison, Wisconsin). iCell® Neurons are human induced pluripotent stem cell (iPSC)-derived neurons that exhibit biochemical, electrophysiological, and pathophysiological properties characteristic of native human neurons. Due to their high purity, functional relevance, and ease of use, iCell® Neurons represent a very useful in vitro test system for neurobiology interrogations in basic research and many areas of drug development.

In some embodiments, a defined media (i.e., a media that does not contain tissue, feeder cells, or cell-conditioned media) may be used to produce neurons or astrocytes from pluripotent cells such as iPS cells.

The medium used to produce neurons or astrocytes from iPS cells may also be essentially free of serum and/or serum-derived growth factors. In a further embodiment, the medium may have or be essentially free of externally added TGFβ superfamily signaling modulators, including positive modulators or inhibitors of BMP signaling and/or Activin/Nodal/TGFβ/GDF signaling. For example, a BMP signaling inhibitor may be dorsomorphin and an Activin/Nodal/TGFβ/GDF signaling inhibitor may be SB431542. In a still further embodiment, the medium may have or be essentially free of other externally added FGF signaling modulators, particularly FGF inhibitors.

Methods may involve the use of pluripotent stem cells as starting material for differentiation, which could be embryonic stem (ES) cells, induced pluripotent stem cells, or embryonic stem cells derived by somatic cell nuclear transfer. In a certain aspect, the pluripotent stem cells may be clonally derived from a single pluripotent stem cell, may comprise a substantial portion of cells clonally derived from a single cell, or may be a pool of multiple populations of cells, wherein each population of cells is clonally derived from a single cell. In a particular aspect, the pluripotent stem cells may be a population of cells, for example, derived from a single cell.

An exemplary process for obtaining pluripotent stem cells from a single cell may comprise incubating a single pluripotent stem cell in medium comprising a ROCK inhibitor or a myosin II inhibitor (e.g., blebbistatin) under conditions to promote cell growth, such as being incubated under adherent culture conditions. Prior to growing the pluripotent stem cells in the suspension culture for aggregate formation, the single pluripotent stem cell as the originating source may be passaged once, twice, three times, four times, or preferably at least five times. In another aspect, the pluripotent stem cells may also be derived from an iPS cell population comprising more than a single cell. The cells may be human, mouse, or other mammalian cells.

Prior to differentiation, the pluripotent stem cells may be cultured on a non-cellular matrix component. Non-limiting examples of the matrix component may include collagen, gelatin, poly-L-lysine, poly-D-lysine, poly-D-ornithine, laminin, RectroNectin®, vitronectin and fibronectin and mixtures thereof, for example, protein mixtures from Engelbreth-Holm-Swarm mouse sarcoma cells (such as Matrigel™ or Geltrex®) and lysed cell membrane preparations (Klimanskaya et al., 2005). To eliminate variation introduced by uncharacterized components, the medium may be essentially free of externally added animal-derived components, such as serum, feeder cells, or animal-derived proteins, wherein the animal is not a human.

The medium may be chemically defined or undefined (i.e., containing externally added, chemically undefined components). A defined medium will have known quantities and chemical compositions of all ingredients. An undefined medium may have some undefined components, like some complex ingredients, such as cellular extract, which consist of a mixture of chemical species in unknown proportions. In a particular example, the defined medium may be based on Dulbecco's Modified Eagle Medium (DMEM), such as a DMEM medium with nutrient mixture F-12 (DMEM/F12), a DMEM/F12 medium with N2 supplement, a DMEM-F12 medium with B-27 supplement, or a DMEM-F12 medium with an insulin, transferrin, and selenium (ITS) supplement.

In some aspects, the cells may be cultured in a priming medium for about 4, 8, or 12 hours, 1, 2, 3, 4, 5, 6, 7, 8, 9, or 10 days (or any range derivable therein) prior to aggregate formation. The cells may be cultured in a priming medium volume of about 5, 10, 15, 20, 25, 30, 50, 100, 150, 200, 250, 300, 350, 400, 450, 500 mL, or any range derivable therein. The cells may be cultured in a priming medium that is replaced every 4, 8, or 12 hours, 1, 2, 3, 4, 5 days, or any range derivable therein. In certain aspects, the cells may be cultured in a priming medium for a priming period. The priming period may be a defined time period or a time period identified by optimization for a selected pluripotent stem cell line or clone or other specified condition(s). For example, the defined priming period may start from about 4, 8, or 12 hours, 1, 2, 3, 4, 5, 6, 7, 8, 9, or 10 days (or any range derivable therein) prior to differentiation or any range derivable therein. The priming period may last about 4, 8, or 12 hours, 1, 2, 3, 4, 5, 6, 7, 8, 9, or 10 days, or continue up to the time when further differentiation starts (any intermediate time period may also be included).

In further aspects, the methods may further comprise culturing the pluripotent stem cells or progeny cells thereof in the presence of a determined amount of externally added TGFβ superfamily signaling inhibitor and/or FGF8. Such culturing may be any time in the steps of priming (culturing prior to aggregate formation), forming aggregates, or further differentiation. In a particular aspect, the cells may be cultured at most about one, two, three, four, five, six days (or any range derivable therein) during priming and/or during aggregate formation in the presence of a determined amount of externally added TGFβ superfamily signaling inhibitor and/or FGF8. In a further particular aspect, the cells may be cultured at most about the first one, two, three, four, five, six, seven, eight, nine, ten days (or any range derivable therein) of further differentiation after aggregate formation in the presence of a determined amount of externally added TGFβ superfamily signaling inhibitor and/or FGF8 and then in the subsequent period cultured in the absence of the externally added TGFβ superfamily signaling inhibitor and/or FGF8. In certain aspects, the cells may be cultured in the presence of a determined amount of externally added TGFβ superfamily signaling inhibitor(s) and/or FGF8 during priming, aggregate formation and/or further differentiation. In certain aspects, the cells may be cultured in the absence of externally added TGFβ superfamily signaling inhibitor and/or FGF8 during priming, aggregate formation and/or further differentiation.

Due to line-to-line and clone-to-clone variability (i.e., cell line and clone variability), methods may be used for determining the appropriate amount of TGFβ superfamily signaling inhibitor and/or FGF8 for neural differentiation of a population of pluripotent stem cells. In a certain aspect, the method may further comprise testing the neural differentiation efficiency of a population of pluripotent stem cells to determine the appropriate amount, if any, of externally added TGFβ superfamily signaling inhibitor(s) and/or FGF8 needed that will result in efficient neural differentiation yielding a neural culture of high purity. The neural differentiation efficiency can be measured in terms of all neurons or neural cell types, such as astrocytes.

The differentiation may start with or without dissociating the pluripotent stem cells. In some embodiments, the differentiation may comprise dissociating the stem cells into an essentially single cell culture. The dissociation encompasses the use of any method known now or later developed that is capable of producing an essentially single cell culture. In an exemplary embodiment, the cells may be dissociated by a protease treatment or a mechanical treatment like pipetting. For example, the protease may be collagenase, trypsin-EDTA, dispase, or a combination thereof. Alternatively, a chelating agent may be used to dissociate the cells, such as sodium citrate, EGTA, EDTA or a combination thereof. An essentially single cell culture may be a cell culture wherein the cells desired to be grown are dissociated from one another, such that the majority of the cells are single cells, or at most two cells that remain associated (doublets). Preferably, greater than 50%, 60%, 70%, 80%, 90%, 95%, 96%, 97%, 98%, 99% or more of the cells desired to be cultured are singlets or doublets.

The differentiation method encompasses the use of any method known now or later developed that is capable of differentiating pluripotent stem cells. The differentiation may involve forming cell aggregates (embryoid bodies) or may not need to form cell aggregates. In a particular embodiment, the dissociated cells may form cell aggregates in a medium (aggregate formation medium). The aggregate formation medium may contain or may be essentially free of TGFβ superfamily signaling modulators and bFGF.

Any of the priming, aggregate formation and/or further differentiation culture media may contain externally added at least or at most from about 5 to about 200 ng/ml FGF8, e.g., at least or about 5, 10, 15, 20, 25, 30, 35, 40, 45, 50, 55, 60, 65, 70, 75, 80, 85, 90, 95, 100, 150, 180, 200 ng/ml or any range derivable therein. Externally added FGF8 or TGFβ superfamily signaling inhibitors may be at an amount of at least, about or at most 5, 10, 15, 20, 25, 30, 35, 40, 45, 50, 55, 60, 65, 70, 75, 80, 90, 100, 150, 200 ng/ml, at least, about, or at most 0.5, 0.6, 0.7, 0.8, 0.9, 1, 1.5, 2, 2.5, 3, 4, 5, 6, 7, 8, 9, 10, 25, 50 μm, or any range derivable therein, or any concentration effective for improving the production of high purity neural cell types.

To promote survival of dissociated cells, the medium may comprise an externally added myosin II inhibitor or Rho-associated kinase (ROCK) inhibitor. The myosin II inhibitor may be blebbistatin. The ROCK inhibitor may be Y27632, HA-100 or H1152. Such inhibitors may have a concentration of about 0.05 to about 50 μm, for example, at least or about 0.05, 0.1, 0.2, 0.5, 0.8, 1, 1.5, 2, 2.5, 5, 7.5, 10, 15, 20, 25, 30, 35, 40, 45, or 50 μm, including any range derivable therein, or any concentration effective for promoting cell growth or survival.

The aggregate formed from the pluripotent stem cells may be about, at least or at most 5, 10, 15, 20, 25, 30, 50, 100, 150, 200, 250, 300, 350, 400, 450, 500 μm in diameter. The diameter may be a mean, median or an average diameter. In another aspect, at least about 20%, 30%, 40%, 50%, 80%, 90%, 95%, or 99% (or any range derivable therein) of the aggregates may comprise at least or about 10, 15, 20, 25, 30, 35, 40, 45, 50, 80, 100, 150, 200, 250, 300, 400, 500, 1000 cells, or any range derivable therein. In certain aspects, a substantial portion (e.g., at least about 50%, 80%, 90%, 95%, 99% or any range derivable therein) of the aggregates are about 80 to 200 μm in diameter. The approximate uniformity of an optimal range of aggregate size may promote differentiation as differentiation is guided by spatial cues and interaction between various cell types, which can be manipulated by varying aggregate size.

The differentiation may comprise culturing pluripotent stem cells and/or progeny cells thereof in an adherent or suspension culture. In a particular embodiment, during differentiation, the cell may be transferred to an adherent culture. For example, the adherent culture may have a non-cellular matrix component. In a preferable embodiment, the methods may be used for differentiation of pluripotent stem cells to produce neural cells in a suspension culture. Pluripotent stem cells or progeny cells thereof may be incubated in a suspension culture. In a further embodiment, pluripotent stem cell aggregates may be formed in a suspension culture. The suspension culture may have a volume of about, at least or at most 2 mL, 5 mL, 10 mL, 20 mL, 30 mL, 40 mL, 50 mL, 100 mL, 200 mL, 500 mL, 1 liters, 3 liters, 5 liters, 10 liters, 20 liters, 25 liters, 30, liters, 40 liters, 50 liters, or any range derivable therein, such as in a bioreactor. Some embodiments involve cells growing in a space whose volume is larger than a standard Petri dish or 96-well plate; consequently, some embodiments exclude the use of such containers.

To optimize the size and growth of the cell aggregates, the suspension culture may be moved at a speed of at least or about 5, 10, 15, 20, 30, 35, 40, 45, 50, 55, 60, 65, 70, 75, 80, 85, 90, 100 rpm, or any range of speed derivable therein. The movement may comprise stirring, shaking, rocking or rotating as non-limiting examples.

The medium used in differentiation may or may not comprise the use of externally added TGFβ superfamily signaling inhibitor(s), bFGF inhibitors, or both. The TGFβ superfamily inhibitor may be a BMP signaling inhibitor and/or Activin/Nodal/TGFβ/GDF signaling inhibitor. A bFGF signaling inhibitor may be PD166866. With the improvement of neural induction by priming, the method may obviate the need to use such inhibitors in differentiation.

In certain aspects, the population of iPS cells or differentiated cells may be clonally derived from a single iPS cell. In a further aspect, there may be provided a cell population of at least or about $10^7$, $10^8$, $10^9$, or up to about $10^{10}$ (or any range derivable therein) cells. The cell population provided may comprise at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% (or any range derivable therein) cells, such as neural cells. In a particular embodiment, the cell population may comprise at least 90%, 91%, 92%, 93%, 94%, 95%, 96%, 97%, 98%, 99% or 100% (or any range derivable therein) neural cells. This invention may achieve an unexpected high yield of neural cells from differentiation of pluripotent stem cells as compared with currently known methods and methods without the use of priming.

A cell population comprising the neural cells or astrocytes provided by any of the methods above may also be provided. Further embodiments may provide an isolated cell population of at least or about $10^6$, $10^7$, $10^8$, $10^9$, $10^{10}$ neural cells (or any range derivable therein). The differentiated cells may comprise at least 90% (for example, at least or about 90%, 95%, 96%, 97%, 98%, 99%, 99.5%, or any range derivable therein) neural cells or astrocytes. In a specific example, the cell population may contain a transgene (e.g., encoding a selectable and/or screenable marker) under a promoter specific for neural cells. For example, the transgene may be an antibiotic resistance gene or a fluorescent protein-encoding gene. Non-limiting examples of neural-specific promoters include a promoter of doublecortin (DCX), neuronal class III β-tubulin (TUJ-1), synapsin 1 (SYN1), enolase 2/neuron-specific enolase (ENO2/NSE), glial fibrillary acidic protein (GFAP), tubulin alpha-1A chain (TUBA1A), neurogenin 2 (NGN2) or microtubule-associated-protein-2 (MAP-2). The method may further comprise isolating or enriching neural cells or astrocytes, for example, based on the neuron-specific or astrocytes-specific expression of selectable or screenable markers.

B. Neuron Lineage Characterization

To identify neural cells, determine differentiation efficiency toward a neural lineage, select for or isolate neural cells, or enrich neural cells, neural lineage characteristics may be assessed (Schwartz et al., 2008).

In particular embodiments, the progenitor neural lineage cells, such as the cultured cells, may be identified as neural cells based on the expression by the cells of one or more of nestin, Sox1, Pax6, FORSE-1, N-CAD, CD133, FOXG1 and 3CB2. Such a culture of cells can be produced by the methods described herein or by other methods including those later developed. In particular embodiments, mature neural cells, including the cultured cells, may be identified as mature neural cells by the expression of one or more of Dcx, MAP-2, Synapsin 1, TuJ1, NSE, Map2a, Gap43, NF, CD24, CDH2/CD325, synaptophysin, and CD56/NCAM. Such a culture of cells can be produced by the methods described herein or by other methods including those later developed.

Neural cells can be characterized according to a number of phenotypic criteria. The criteria include but are not limited to microscopic observation of morphological features, detection or quantification of expressed cell markers, enzymatic activity, neurotransmitters and their receptors, and electrophysiological function.

Certain cells that may be used various embodiments have morphological features characteristic of neuronal cells. These features are recognized by those of skill in the art. For example, neurons include small cell bodies, and multiple processes reminiscent of axons and dendrites.

Neural cells can also be characterized according to whether they express phenotypic markers characteristic of particular kinds of neural cells including but not limited to dopaminergic neurons (markers include TH, AaDC, Dat, Otx-2, FoxA2, LMX1A and VMAT2), cholinergic neurons (markers include NGF, ChAT), GABAergic neurons (markers include GAD67 and vGAT), glutamatergic neurons (markers include vGLUT1), serotonergic neurons, motor neurons (markers include HB9, SMN, ChAT, NKX6), sensory neurons (markers include POU4F1 and peripherin), astrocytes (markers include GFAP and Tapal), and oligodendrocytes (markers include O1, O4, CNPase, and MBP). The neural cells may express 1, 2, 3, 4, 5, or more markers of a particular kind of neural cell type.

Also characteristic of specific neural subtypes, particularly terminally differentiated cells like dopaminergic, GABAergic, glutamatergic, serotonergic, and cholinergic neurons, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained, e.g., by detecting receptors for gamma amino butyric acid (GABA), glutamate, dopamine, 3,4-dihydroxyphenylalanine (DOPA), noradrenaline, acetylcholine, and serotonin.

In a particular aspect, astrocytes may be cultured or co-cultured with neurons. Astrocytes are a sub-type of glial cells in the central nervous system. They are also known as astrocytic glial cells. Generally star-shaped, their many processes typically envelope synapses made by neurons in vivo. Astrocytes are classically identified using histological analysis; many of these cells express the intermediate filament glial fibrillary acidic protein (GFAP). Three forms of astrocytes exist in the CNS, fibrous, protoplasmic, and radial. The fibrous glia are usually located within white matter, have relatively few organelles, and exhibit long unbranched cellular processes. This type often has "vascular feet" that physically connect the cells to the outside of capillary walls when they are in close proximity to them. The protoplasmic glia are found in grey matter tissue, possess a larger quantity of organelles, and exhibit short and highly branched tertiary processes. The radial glia are disposed in a plane perpendicular to the axis of ventricles. Radial glia are predominantly present during development and can play a role in neuron migration in vivo. Mueller cells of retina and Bergmann glia cells of cerebellar cortex represent an exception, and are still present during adulthood.

C. Genetic Alteration of Cells

The cells used in various aspects as described herein (e.g., neurons, astrocytes, etc.) can be made to contain one or more genetic alterations by genetic engineering of the cells either before, during, or after differentiation (U.S. Pat. Pub. 2002/0168766). Generally, a cell is "genetically altered" or "transgenic" when a polynucleotide has been transferred into the cell by any suitable means of artificial manipulation, or where the cell is a progeny of the originally altered cell that has inherited the polynucleotide. For example, the cells can be processed to increase their replication potential by genetically altering the cells to express telomerase reverse transcriptase, either before or after they progress to restricted developmental lineage cells or terminally differentiated cells (US 2003/0022367). In another example, the cells may comprise a screenable or selectable marker under the control of a neural promoter (e.g., the MAP2 promoter), allowing for efficient selection or screening of neuronal cells. In particular, pluripotent cells can be engineered with the marker, differentiated into neural cells, and then selected based upon the marker to achieve a purified population of neural cells (e.g., neurons, dopaminergic neurons, serotoninergic neurons, glutamatergic neurons, GABA neurons, etc.).

IV. Use of Neural Cultures

Cultures of neural cells that display synchronous neuron firing or synchronous action potentials can also be used, e.g., in testing the effect of molecules on neural differentiation or survival, or in toxicity testing or in testing molecules for their effects on neural or neuronal functions. This can include screens to identify compounds that affect neuron activity, plasticity (e.g., long-term potentiation), or function. The cell cultures may be used in the discovery, development and testing of new drugs and compounds that interact with and affect the biology of neural stem cells, neural progenitors or differentiated neural or neuronal cell types. The neural cells can also have great utility in studies designed to identify the cellular and molecular basis of neural development and dysfunction including but not limited to axon guidance, neurodegenerative diseases, neuronal plasticity and learning and memory. Such neurobiology studies may be used to identify novel molecular components of these processes and provide novel uses for existing drugs and compounds, as well as identify new drug targets or drug candidates.

In some embodiments, one or more specific compounds may be tested to determine if the compound has effects that may be beneficial for the treatment of a disease. For example, the ability of a compound to alter neural network activity such as synchronous bursting may be used by exposing a culture comprising excitatory and inhibitory neurons, optionally also comprising astrocytes, wherein the excitatory neurons, inhibitory neurons, and/or astrocytes are derived from iPS cells obtained from a healthy donor. Based on the effects of the compound on neural activity, one may then be able to determine if the compound may be useful for the treatment of a disease. For example, a compound that is shown to reduce synchronous firing of neurons may be useful for the treatment of a disease characterized by too much synchronous firing (e.g., epilepsy, autism, schizophrenia, etc.). In some embodiments, the excitatory neurons, inhibitory neurons, and/or astrocytes are derived from iPS cells from a subject that has a disease (e.g., a genetic disease or a disease with a genetic component or risk factor) such as a neuorological or neurodegenerative disease (e.g., autism, epilepsy, ADHD, schizophrenia, bipolar disorder, etc.). In some embodiments, neurons may be cultured in the presence of a first compound or toxin so that the neural culture will display properties similar to a disease state; in these embodiments, a second compound may be provided to the neural cultures to see if the second compound can alleviate or reduce the effect of the first compound or toxin. In other embodiments, neural cultures may be used to determine if a compound produces toxicity or adverse effects on the neural culture.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Extracellular Single-Unit Recordings of Neurons from iPS Cells on the Mestro Multielectrode Array The following methods may be used to culture neural cells on a Mestro Multielectrode Array (MEA). iCell® Neurons are thawed and plated into a 48-well MEA plate pre-coated with 50% Polyethyleneimine (PEI; Sigma) solution. On day 1 post-plating, 100% of spent medium is replaced with Neurobasal-A medium (NBA; Life Technologies) +10% KnockOut Serum Replacement (KSR; Life Technologies). On day 5 post-plating, 50% of spent medium is replaced with NBA +10% KSR. On day 8 post-plating, baseline activity is recorded, cells are treated with compounds, and the activity is subsequently recorded.

Preparing the 48-well MEA Plate:
1. Prepare 1 l of borate buffer by dissolving 3.10 g of boric acid and 4.75 g of sodium tetraborate in distilled water. Adjust the pH to 8.4. Scale volumes, if necessary.
2. Prepare a 0.05-0.1% PEI solution by diluting 50% PEI solution in borate buffer. Filter the 0.05-0.1% PEI solution through a 0.22 µm filter. Note: 0.05-0.1% PEI solution can be stored at 4° C. for up to 1 month.
3. Add 125 µl/well of 0.05-0.1% PEI solution to the 48-well MEA plate. Incubate at room temperature for 1 hour.
4. Aspirate the PEI solution from the 48-well MEA plate. Do not allow the wells to dry.
5. Rinse 4 times with at least 300 µl/well of sterile water.
6. Air-dry the 48-well MEA plate with the lid off in a sterile biological safety cabinet overnight. The 48-well MEA plate can be allowed to air-dry overnight to achieve optimal cell attachment and maximal performance.

Thawing iCell® Neurons: The following procedure details thawing 1 vial of iCell® Neurons into a 48-well MEA plate. Scale volumes accordingly for 2 vials of iCell® Neurons. Do not prepare more than two 48-well MEA plates at one time.
1. Prepare Complete iCell® Neurons Maintenance Medium (Complete Maintenance Medium) according to the iCell® Neurons User's Guide. Optionally, penicillin-streptomycin can be added to Complete Maintenance Medium at 1× final concentration.
2. Dilute the stock laminin solution (1 mg/ml) by adding 250 µl laminin into 25 ml Complete Maintenance Medium to a final concentration of 10 µg/ml. Gently mix by inverting the tube. Stock laminin solution can be thawed at room temperature or at 4° C. overnight.
3. Thaw iCell® Neurons according to the User's Guide and dilute the cell suspension to a final volume of 10 ml in Complete Maintenance Medium containing 10 µg/ml laminin.
4. Optionally, one can remove a sample of the cell suspension and count the neurons using a hemocytometer to determine the viability and total number of cells.
5. Transfer the cell suspension to a 15 ml centrifuge tube.
6. Concentrate the neurons by centrifuging at 380×g for 5 minutes.
7. Aspirate the supernatant to just above the cell pellet, leaving approximately 50 µl, being careful not to disturb the pellet. This volume approximation is provided due to the imprecise nature of vacuum aspiration.
8. Add 125 µl of Complete Maintenance Medium containing 10 µg/ml laminin to the cell pellet and resuspend gently by pipetting up and down.
9. Measure the total volume of cell suspension with a pipettor. Add Complete Maintenance Medium containing 10 µg/ml laminin to reach a final volume of 220 µl. Mix by gently pipetting.
10. Transfer the cell suspension to a 1.5 ml centrifuge tube.

Plating iCell® Neurons into the 48-well MEA Plate:
1. Thoroughly mix the cell suspension by gently inverting the tube 2-3 times. Tilt the 48-well MEA plate at an angle so that the bottom of all wells are visible. Immediately dispense a 4 pl/well droplet of the cell suspension directly over the recording electrode area of the well of the 48-well MEA pre-coated with PEI solution.
2. Add 2 ml of sterile water to the area surrounding the wells of the 48-well MEA plate to prevent droplet evaporation. Do not allow water into the wells of the 48-well MEA plate. The water may be added after plating the cell suspension to avoid water leaking into wells when the plate is tilted. The exact volume of water may not be critical as long as the 48-well MEA plate maintains a moist environment.
3. Cover the 48-well MEA plate with a sterile MicroClime Environmental lid and incubate in a cell culture incubator at 37° C., 5% CO2, 95% humidity for about 40 minutes.
4. Before adding medium, load a 12-channel pipettor with sterile tips and remove tips as needed to accommodate dispensing into a 48-well MEA plate.
5. Tilt the plate at a steep angle (~75-80 degrees). Gently add 150 µl/well of Complete Maintenance Medium containing 10 µg/ml laminin down the side of the well of the 48-well MEA plate one row at a time using the 12-channel pipettor. Adding the medium too quickly may dislodge the adhered neurons. Timing may be critical in this step. The performance may be compromised if the droplets are allowed to dry. A small volume of medium may be added to all wells first rather than adding the total volume in each well at once.
6. Slowly return the 48-well MEA plate to a flat position on the surface of the biological safety cabinet to allow the medium gently to cover the droplet.
7. Repeat step 5 to reach a final volume of 300 µl/well.
8. Cover the 48-well MEA plate with a sterile MicroClime Environmental lid and incubate in a cell culture incubator at 37° C., 5% CO2, 95% humidity.

Maintaining iCell® Neurons on the 48-well MEA Plate:
1. Prepare NBA medium supplemented with 10% KSR and 1× penicillin-streptomycin (NBA+KSR medium). Filter through a 0.22 µLm filter. Optionally, penicillin-streptomycin can be added to the medium at 1× final concentration.
2. On day 1 post-plating, equilibrate the NBA+KSR medium to 37° C. in a water bath.
3. Load a 12-channel pipettor with sterile tips as detailed above for dispensing and remove the spent medium from the 48-well MEA plate one row at a time.

4. Gently add 150 µl/well of 37° C. NBA+KSR medium to the side of the well of the 48-well MEA plate one row at a time using the 12-channel pipettor. Adding the medium too quickly will dislodge the adhered neurons.
5. Repeat step 4 to reach a final volume of 300 µl/well.
6. Cover the 48-well MEA plate with a sterile MicroClime Environmental lid and incubate in a cell culture incubator at 37° C., 5% CO2, 95% humidity for 4 days.
7. On day 5 post-plating, replace 50% of spent medium (150 µl/well) with 150 µl/well of fresh 37° C. NBA+KSR medium.
8. Incubate in a cell culture incubator at 37° C., 5% CO2, 95% humidity for 3 days. For optimal performance, data acquisition can be performed on day 8 post-plating.

Data analysis and acquisition may be performed using AxIS Software (Axion Integrated Studio, Axion BioSystems). At or after day 8 post-plating, the neuronal preparation may be suitable for data acquisition. Data acquisition can include a pre-application recording (baseline), a compound application recording, followed by a post-application recording (dose). Electrical activity may be acquired using the AxIS Software. The CDIneuronconfig.datastream file can ensure the appropriate data acquisition settings are loaded into the AxIS Software.

Example 2

Modulating Neural-Network Bursting and Synchronicity by Titrating the E/I Ratio using Human iPSC-Derived Cell Types iCell® Neurons: The inventors have utilized iPSC technology to reprogram adult cells from either normal healthy or disease-specific donors back to a pluripotent state. Here in this state, iPS cells have the ability to differentiate into virtually any cell type—including previously inaccessible human neurons. Importantly, iCell® Neurons are provided as cryopreserved material that can be thawed and used any day of the week. A general schematic for the generation of cryopreserved iCell® Neurons is shown in FIG. 1.

Figure 2:
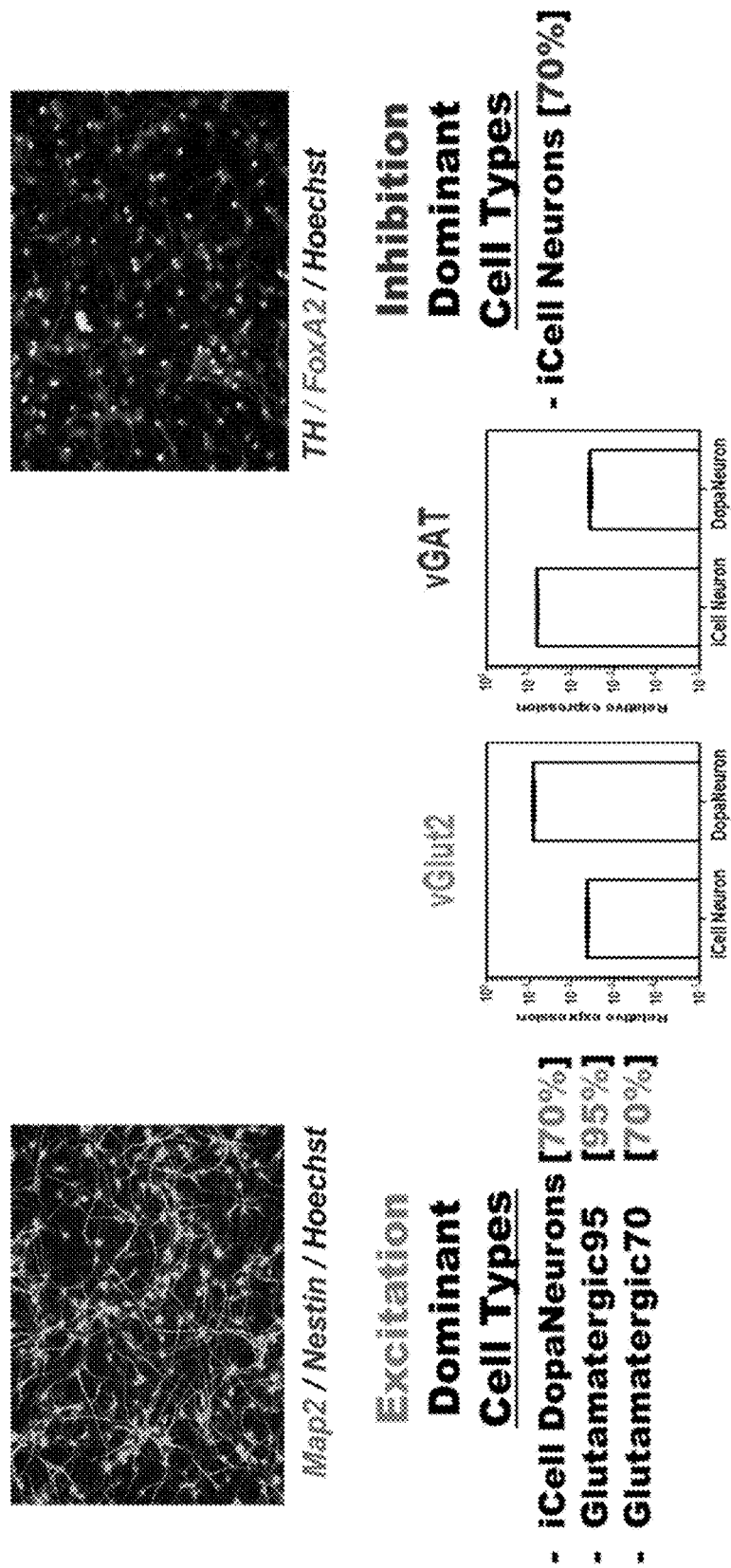
FIG. 2: Example neural cell types of varying quantities of excitatory-to-inhibitory cells.

Features of the cell sample are highlighted as follows. iCell® Neurons are a highly pure population (>95%) of human iPSC-derived cortical neurons, based on positive βIII-tubulin and nestin-negative staining They possess the classical neuronal morphology, with bipolar or multi-polar neurite outgrowths that begin right at Day 1 in culture. These cells have been determined to be a mixture of both inhibitory (GABAergic; ~70%) and excitatory (glutamatergic; ~30%) neurons, and they have been analyzed at the gene expression level and by phenotypic analysis for characteristic molecular markers.

iCell® DopaNeurons: Dopaminergic (DA) neurons can be cultured for an extended period of time. After two weeks, there is a significant degree of neurite outgrowth and the sophisticated network formed at this point is reminiscent of a classical neuronal phenotype. iCell® DopaNeurons are >80% TH-positive. iCell® DopaNeurons are also a mixture of both inhibitory (GABA; ~30%) and excitatory (glutamatergic; ~70%) neurons. Immunohistochemistry was used to confirm neurons as excitatory neurons or inhibitory neurons (FIG. 2).

In these experiments, iCell® DopaNeurons, iCell® Neurons, and iCell® Astrocytes were obtained from Cellular Dynamics International, Inc. (Madison, Wis.), mixed and cultured on MEA plates as described in Example 1. Cells were cultured in BrainPhys media (Bardy et al., 2015) obtained from the Salk Institute (La Jolla, Calif.).

In these experiments, neuronal cell types were mixed to titrate the E/I ratio after each individual cell type was re-suspended and just prior to dotting. For example, if a mixture of 50% iCell® DopaNeurons was mixed with 50% iCell® Neurons, 40 microliters (uL) of the re-suspended iCell® DopaNeurons was mixed with 40 uL of the re-suspended iCell® Neurons. After mixing the cell types was completed, this mixture solution was used to dot the MEA plate.

Figure 10:
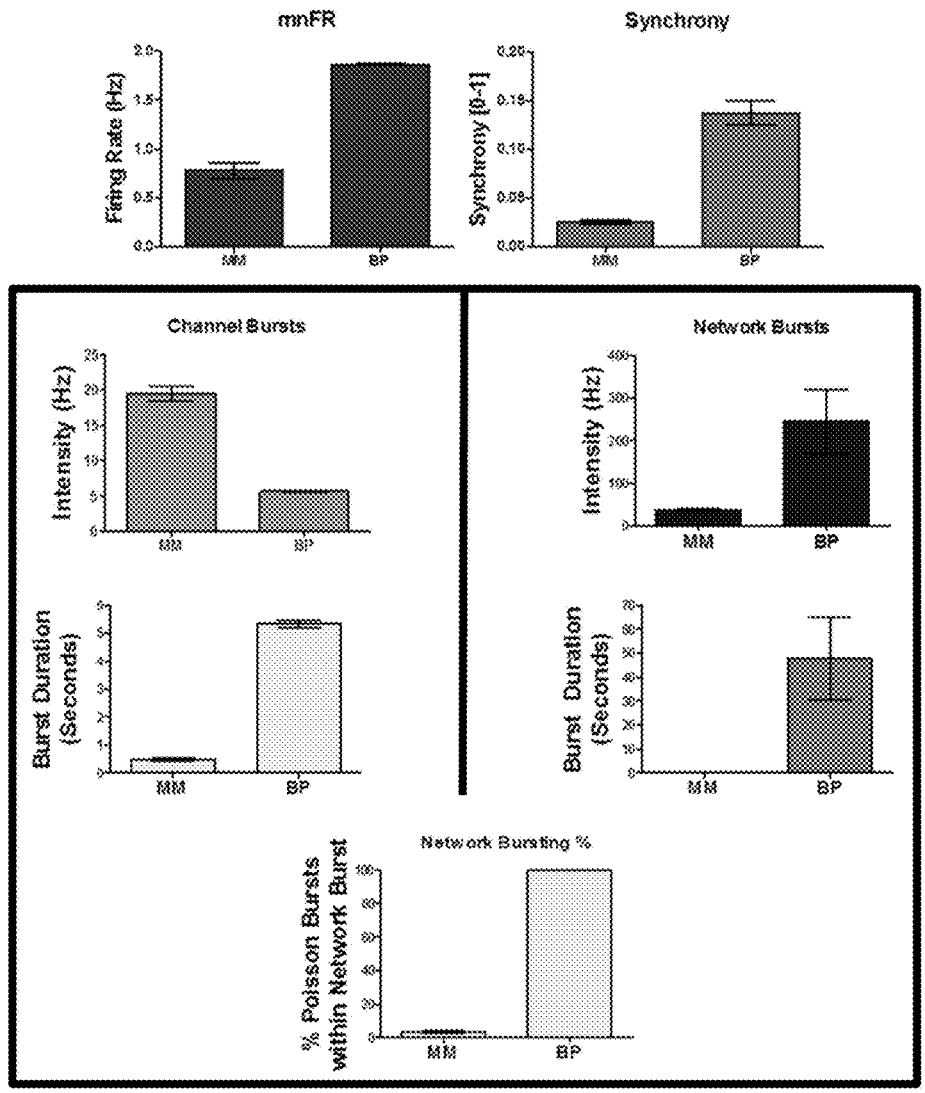
FIG. 10: Network-bursting analysis of iCell® DopaNeurons cultures (~Day 12) (bursting example.

Brain Phys Medium helps build/stabilize Neuronal Networks iCell® DopaNeurons were cultured in either maintenance medium (MM) or Brain Phys (BP) medium for ~12 days, post-thaw. Analysis of bursting dynamics, which depict neuronal-network activity/connectivity, showed that BP-treated cultures displayed a more robust, stabilized large-network bursting, as compared to cultures grown in MM. More specifically, network behaviors shifted from having strong, small-network (single-channel) bursts without larger-network activity seen in MM, to large, whole culture-encompassing (all-channel) network bursts, which still included strong, small-network (single-channel) bursting, in cultures treated with BP. Analysis and results are shown in FIG. 10.

Titrating E/I Ratios: E to I is De-Synchronizing

Figure 3:
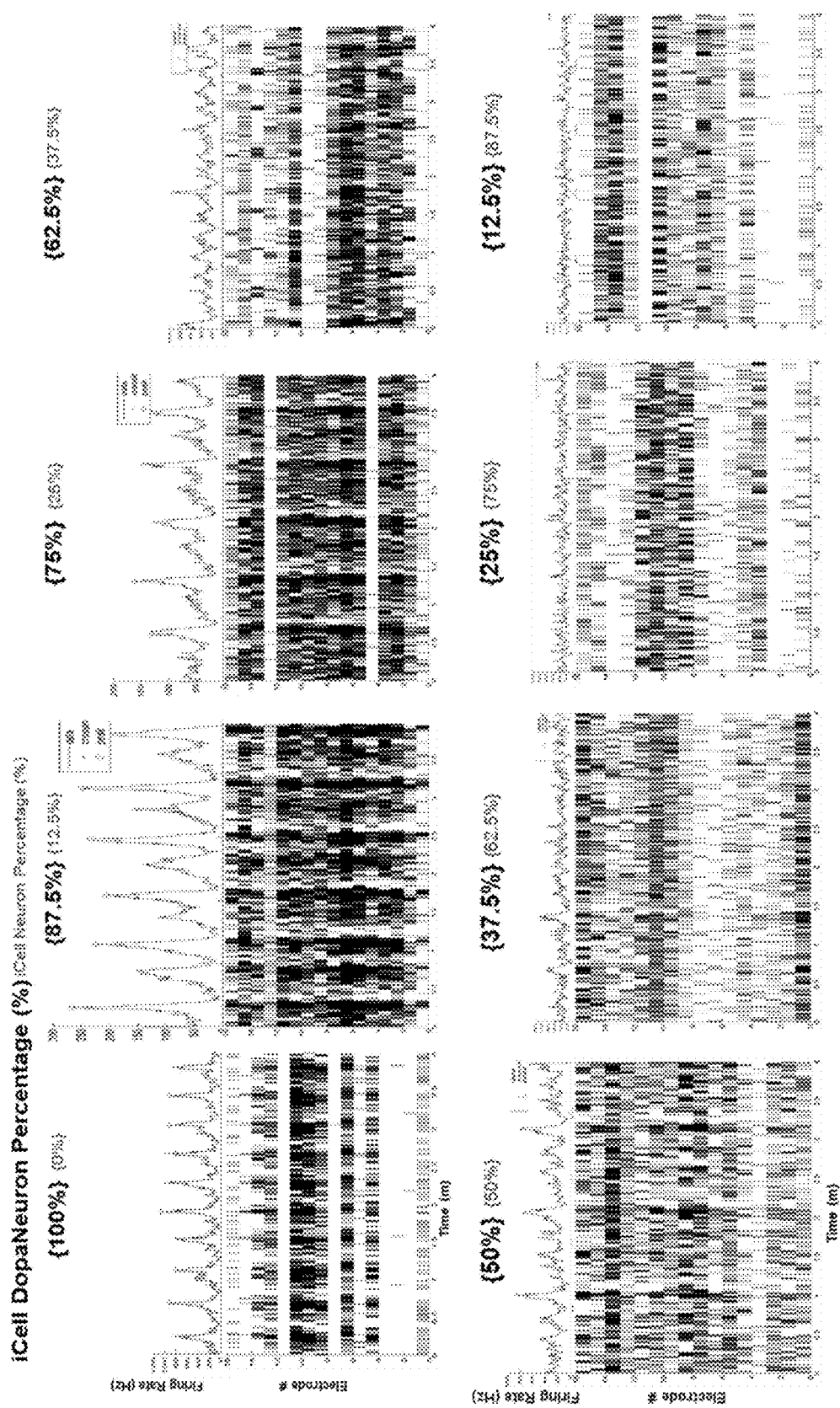
FIG. 3: Example raster plots and velocity graphs of 8 wells with increasing amounts of inhibition. E/I ratios were set by mixing iCell® DopaNeurons (70:30, E:I %) with iCell® Neurons (30:70) (% of cell types are presented above graphs). Velocity graphs represent the instantaneous mean firing rate for each 500 milliseconds of a 4 minute recording Synchronous network bursting begins on Day 6-10 in culture.

Example raster plots and velocity graphs of 8 wells with increasing amounts of inhibition. E/I ratios were set by mixing iCell® DopaNeurons (70:30, E:I %) with iCell® Neurons (30:70) (% of cell types are presented above graphs). Velocity graphs represent the instantaneous mean firing rate for each 500 milliseconds of a 4 minute recording. Synchronous network bursting begins on Day 6-10 in culture. Results are shown in FIG. 3.

Figure 4:
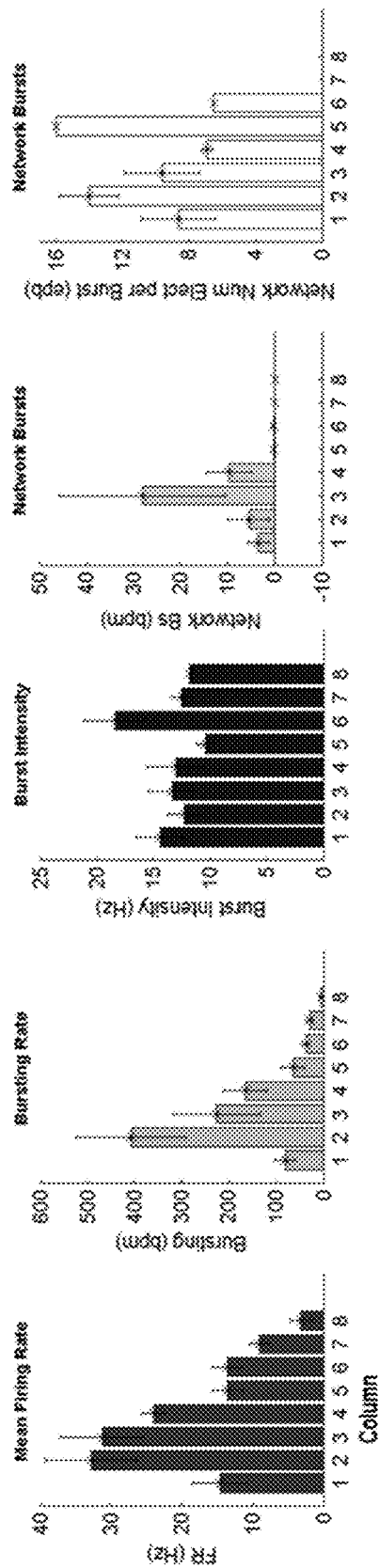
FIG. 4: Axion's 48-well (16 channels per well) MEA plate was used to titrate excitation (iCell® DopaNeurons) with increasing amounts of inhibition (iCell® Neurons) in 8 steps with 6 replicates. Axion's Neural Metrics analysis toolbox was used to assess (per channel) the average mean firing rate, channel bursting rate (poisson surprise) and burst intensity, as well as (all channels) network bursting and the number of channels included within each network burst (expansion). Mean and SEM for all 8 conditions (N=6) are shown for each measure. Decreasing firing rate and bursting rate with increasing amounts of inhibition without altering the intensity of the bursts was observed. Increased inhibitory ratios also shunt network bursting and expansion.

Axion's Neural Metrics analysis toolbox assesses (per channel) the average mean firing rate, channel bursting rate (poisson surprise) and burst intensity, as well as (all channels) network bursting and the number of channels included within each network burst (expansion). Using this toolbox, activity was assessed in all wells of the described mixed cultures. Note the decreasing firing rate and bursting rate with increasing amounts of inhibition, while inhibition did not alter the intensity of each burst. Network bursting is completely abolished with increased amounts of inhibition. Results are shown in FIG. 4.

Titrating E/I Ratios: I to E is Hyper-Synchronizing

Figure 5:
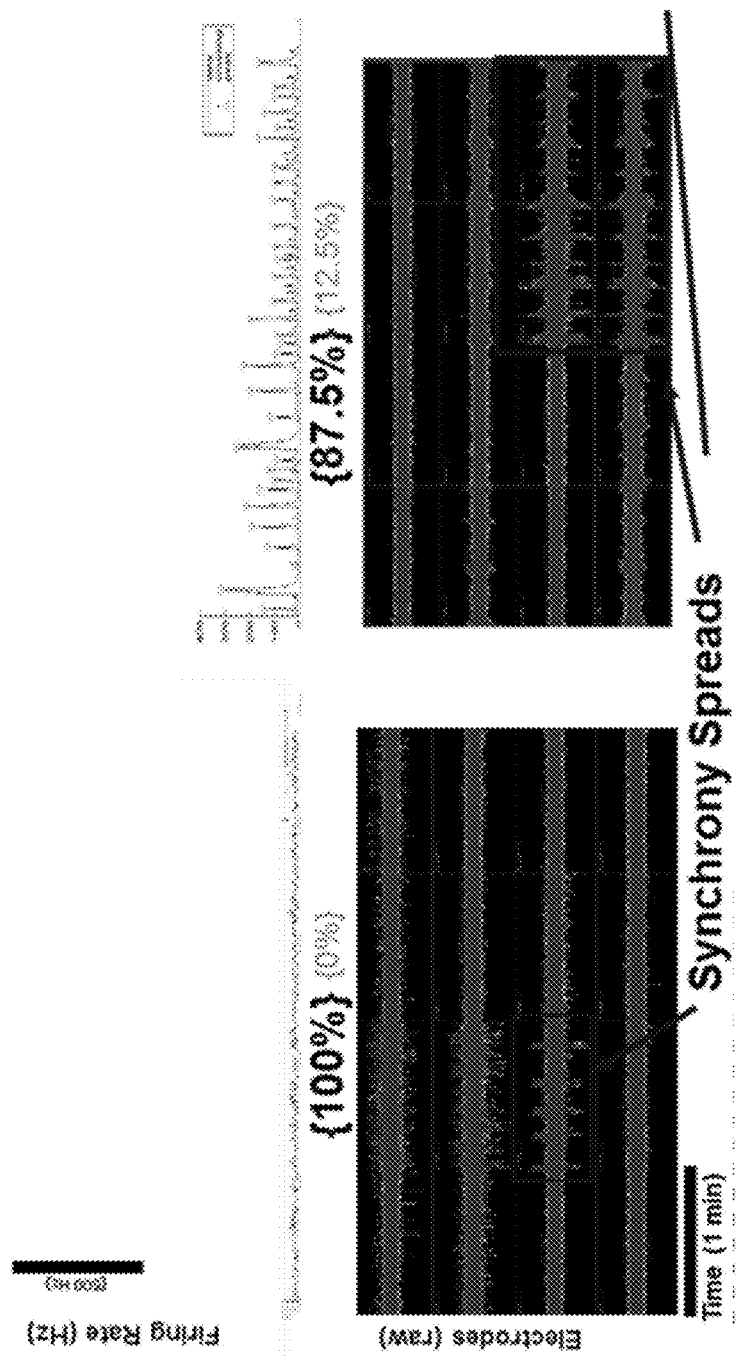
FIG. 5: Example raw data traces and velocity graphs for 8 wells with increasing amounts of excitation are shown. E/I ratios were set by mixing iCell® Neurons (30:70) with Glutamatergic95 (95:5) cells. The expansion (boxes) and increased intensity of network bursts were observed with increasing excitation. The appearance of network seizures was observed after a threshold of excitation was reached (5.) that continued until the culture was observed to be mostly silent at the highest excitatory ratio (8.). For each graph, the percentage of the iCell® Neurons (left, larger font) and the percentage of Glutamatergic95 (right, smaller font) are shown.
Figure 5:
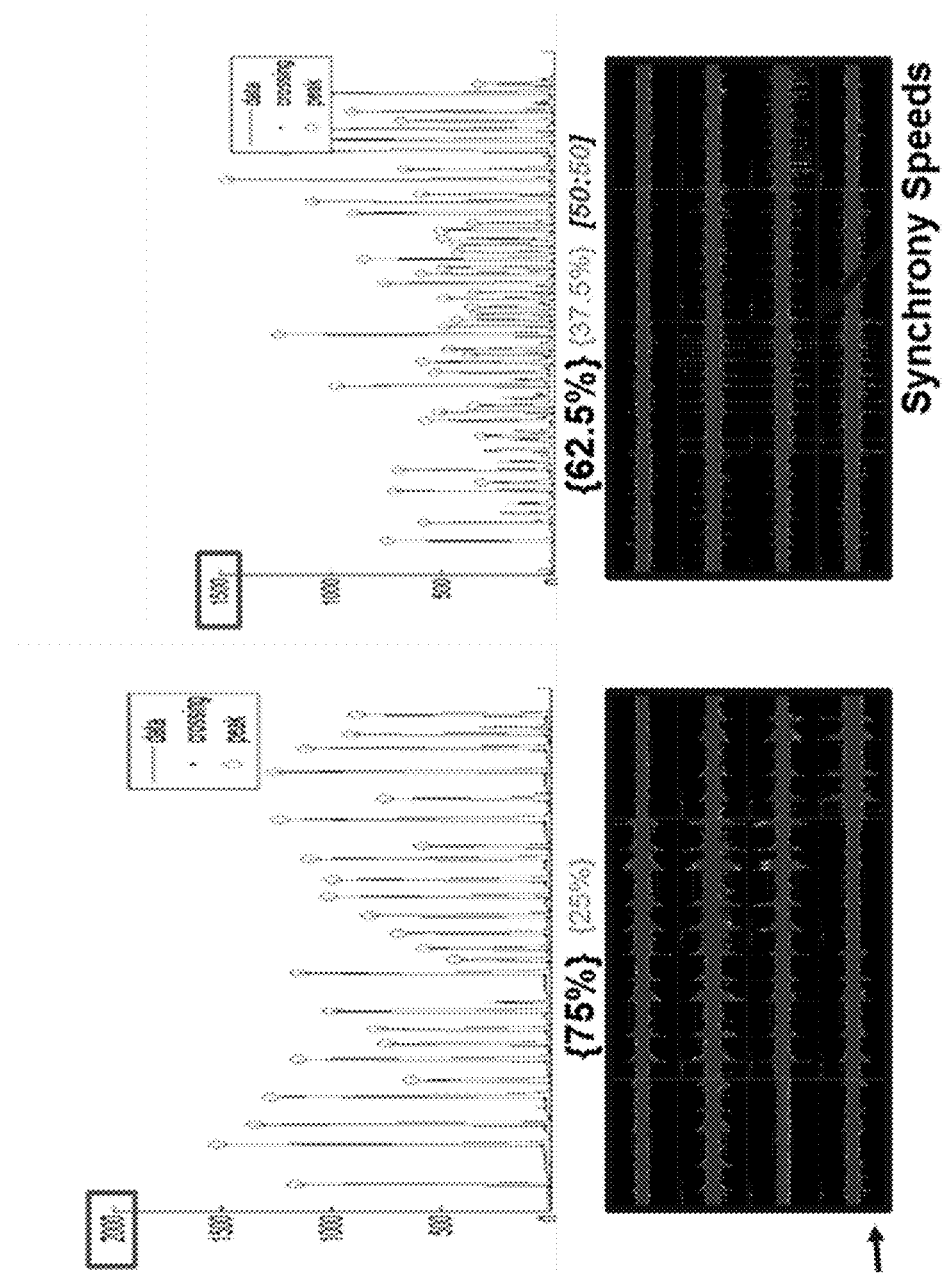
Figure 5:
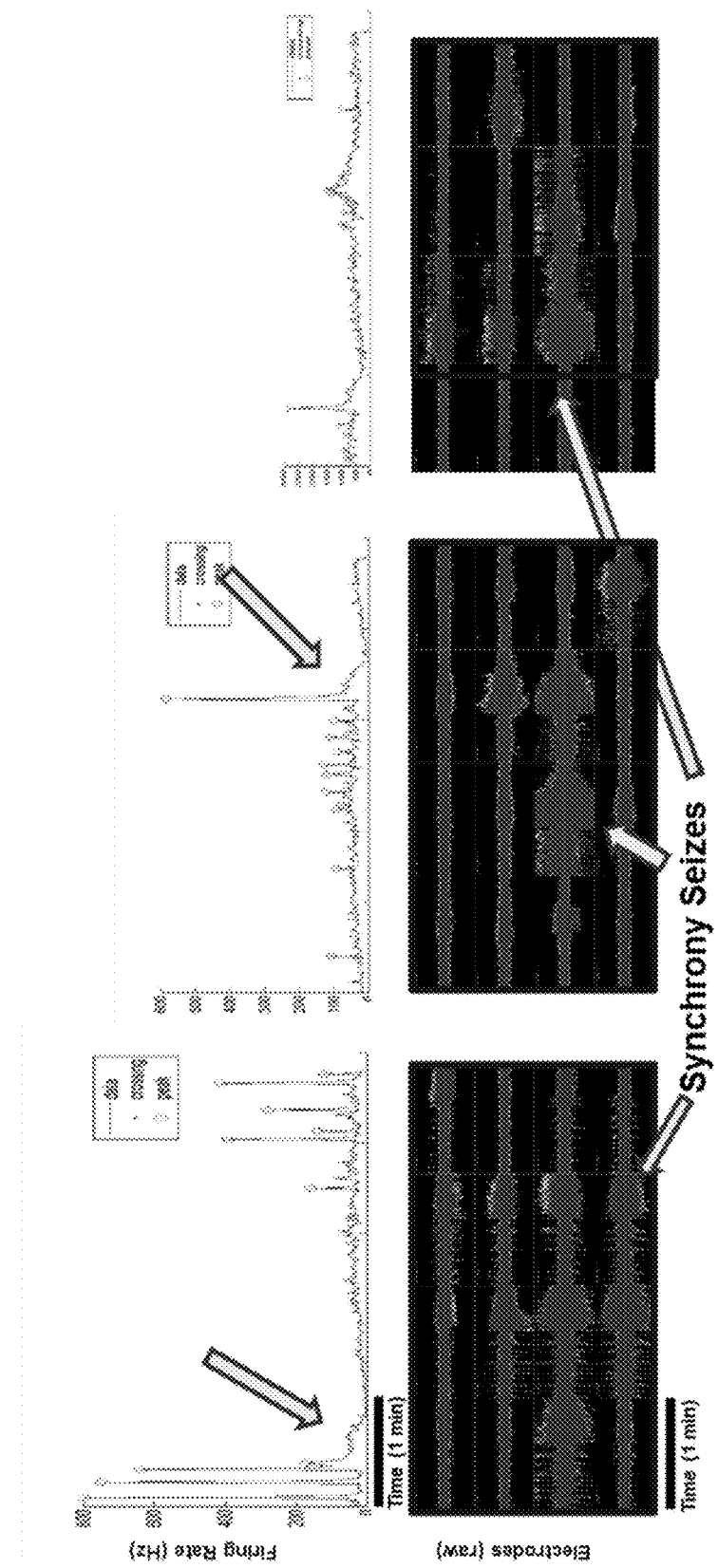
Figure 5:
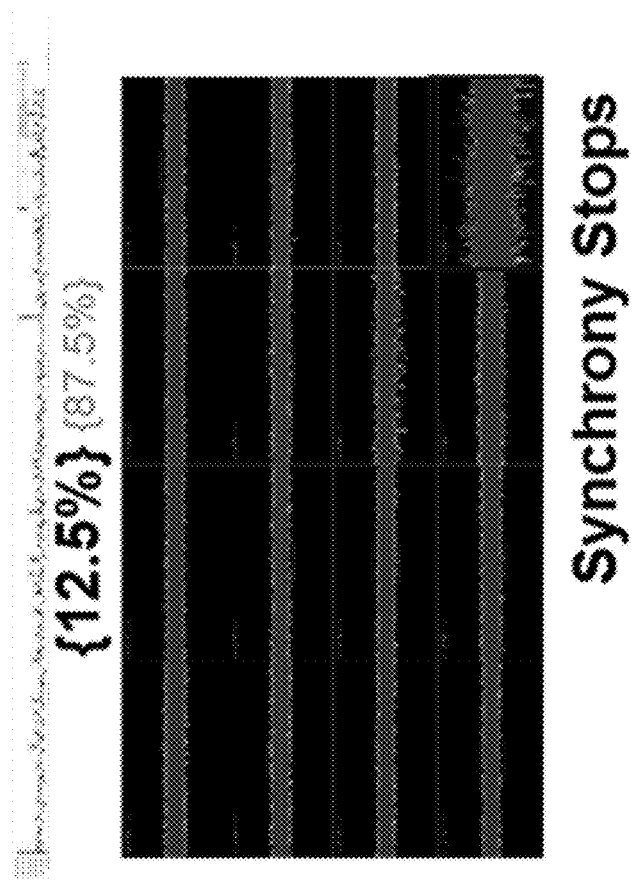

Example raw data traces and velocity graphs of 8 wells with increasing amounts of excitation. E/I ratios were set by mixing iCell® Neurons (30:70, E:I %) with Glutamatergic95 (95:5, E:I %) cells. Cultures continue to display synchronous network bursting for multiple weeks. Note the expansion (FIG. 5, boxes) and increased intensity of network bursts with increasing excitation. Also note the appearance of network seizures after a threshold of excitation is reached. Results are shown in FIG. 5.

Figure 6:
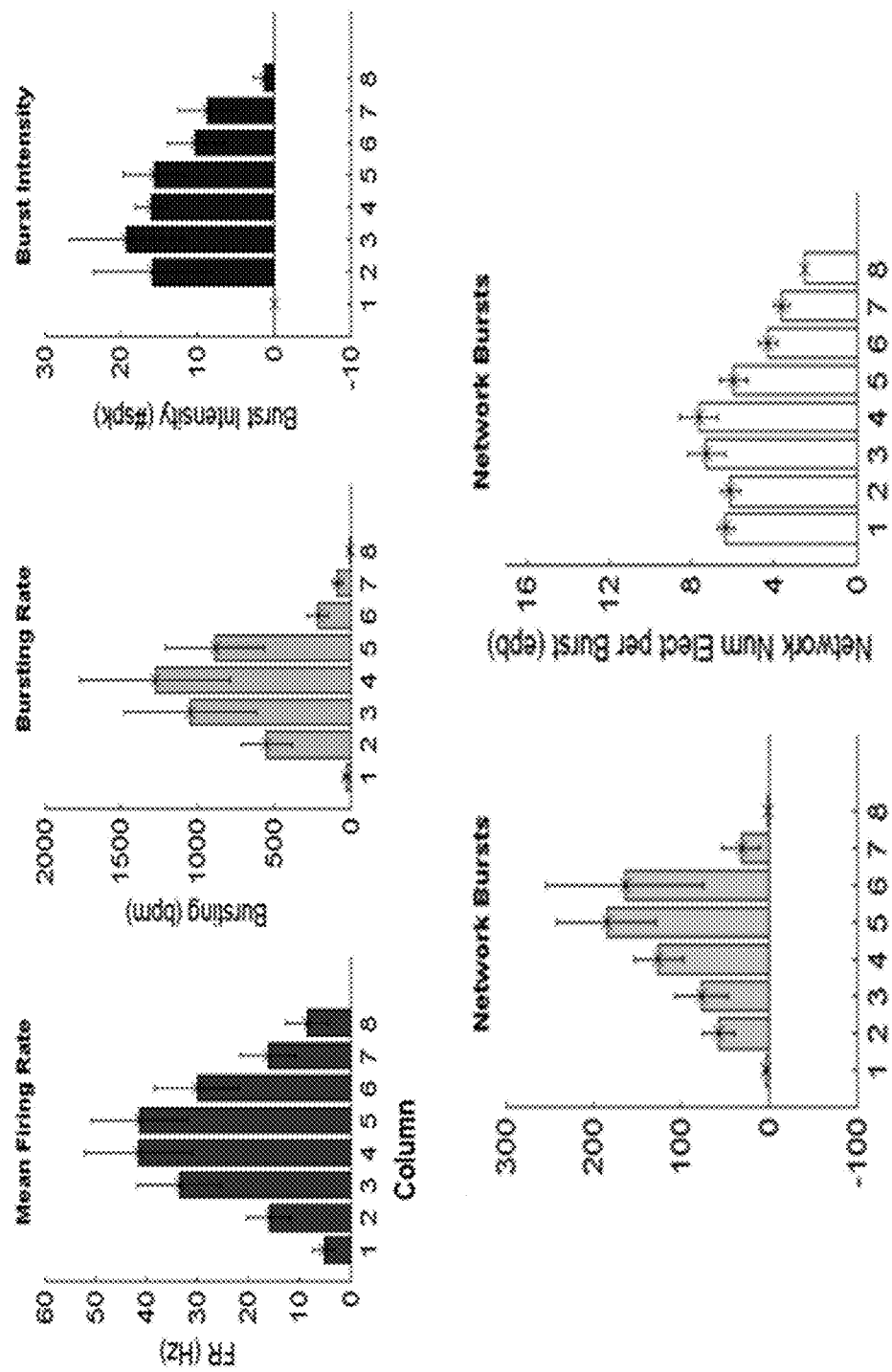
FIG. 6: Axion's 48-well plate allows for 8 conditions with 6 replicates. Average mean firing rate, channel bursting rate and burst intensity all show different E/I ratio peaks and distributions. Channel bursting and intensity drop off with increasing excitation levels. Note that expansion levels, which are consistent at lower amounts of excitation, also drops off with excessive excitation.

Average mean firing rate, channel bursting rate and burst intensity all showed different E/I ratio peaks and distributions. Channel bursting and intensity drop off with increasing excitation levels. Note that expansion levels, which remained constant at lower amounts of excitation, also drop off with excessive excitation. Results are shown in FIG. 6.

Neural Networks Containing Astrocytes is Stabilizing

Figure 7:
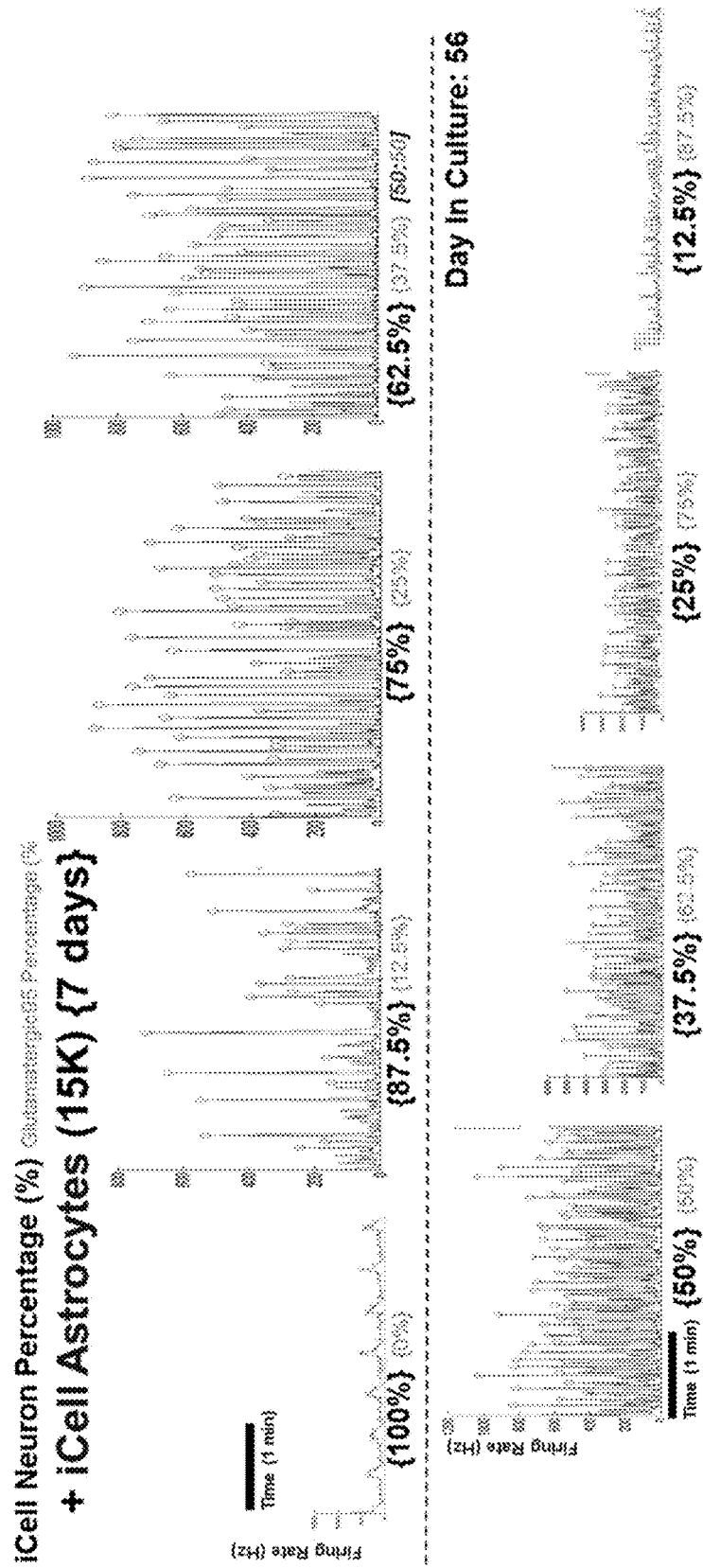
FIG. 7: Same cultures as presented in FIG. 5, 7 days after the addition of ~15 k iCell® Astrocytes.
Figure 8:
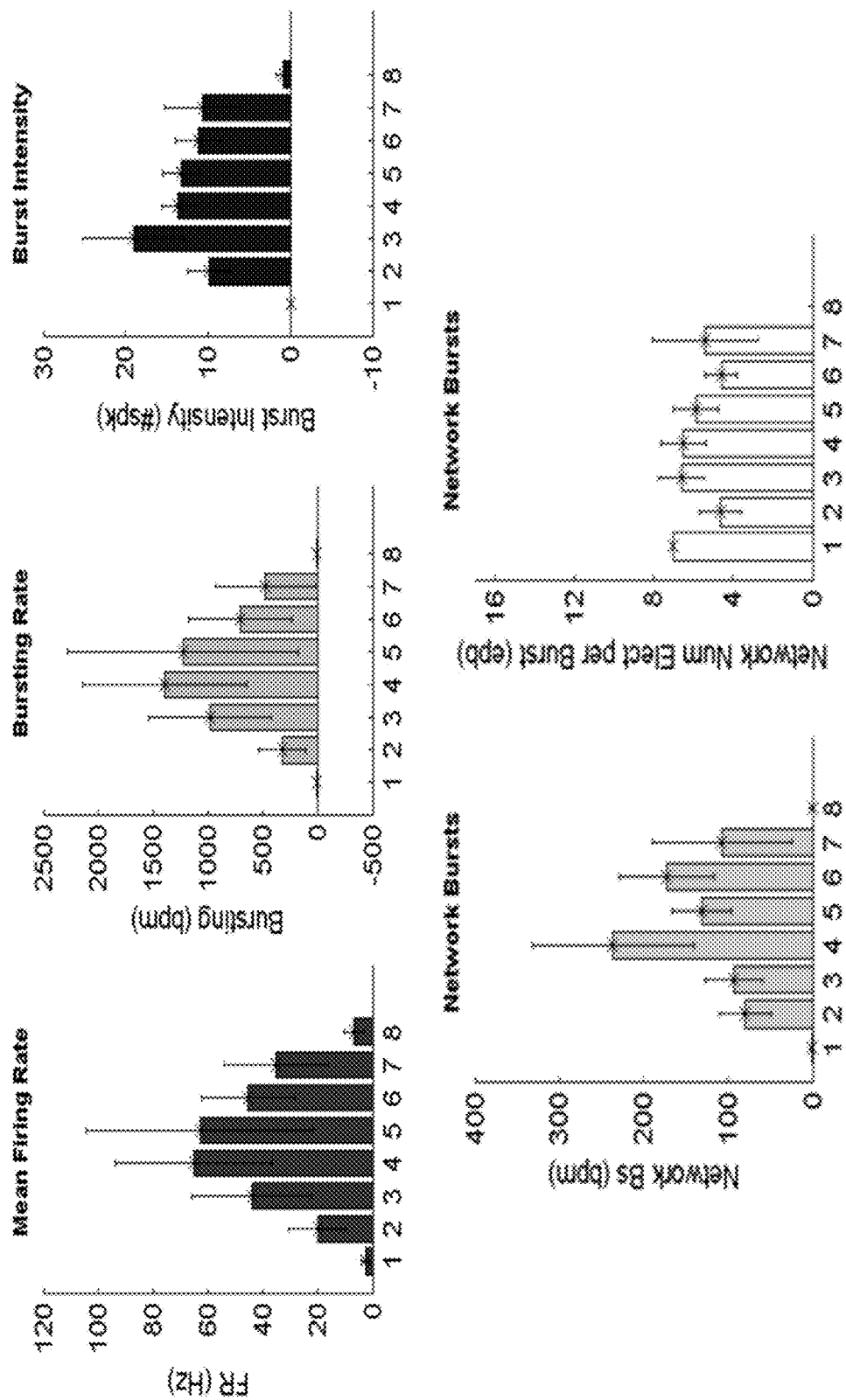
FIG. 8: Channel bursting rate E/I ratio distribution shifted and intensity, network bursting and expansion levels across all E/I ratios normalized following astrocyte addition.

The same cultures as were used in the Titrating E/I ratios were used, with the exception that iCell® Astrocytes were added to the cell culture. Results 7 days after the addition of iCell® Astrocytes are shown in FIG. 7. Channel bursting rate E/I ratio distribution shifted and intensity, network bursting and expansion levels across all E/I ratios normalized following astrocyte addition. Results are shown in FIG. 8.

Figure 9:
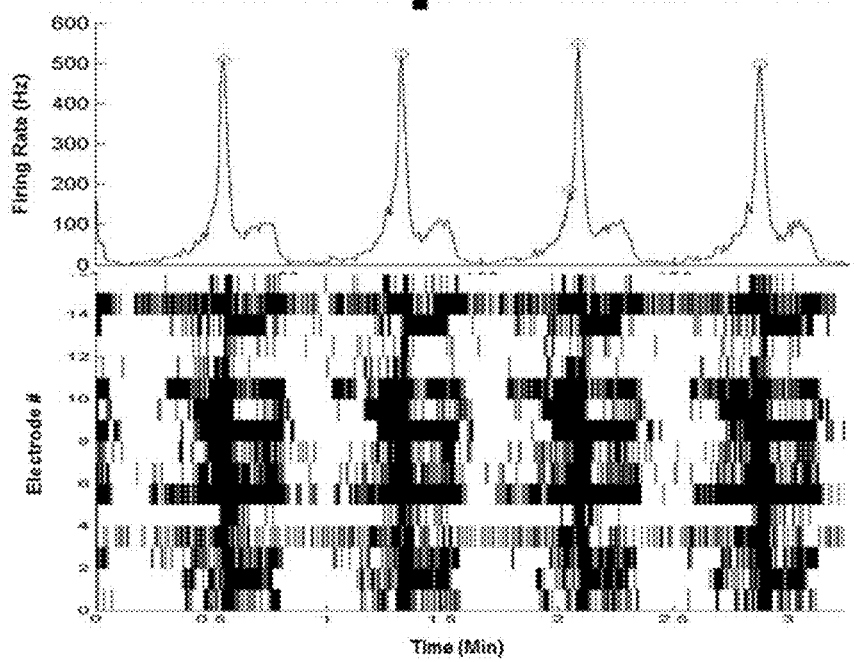
FIG. 9: Two examples of neuronal cultures (Day 12) that express similar E/I ratios (70:30). iCell® DopaNeurons (top) are midbrain neurons, while the Glutamatergic70 (bottom) cell type are cortical neurons. Note both networks display similar network burst intensity levels and a post-burst rumbling level, which is more pronounced in iCell® DopaNeurons.
Figure 9:
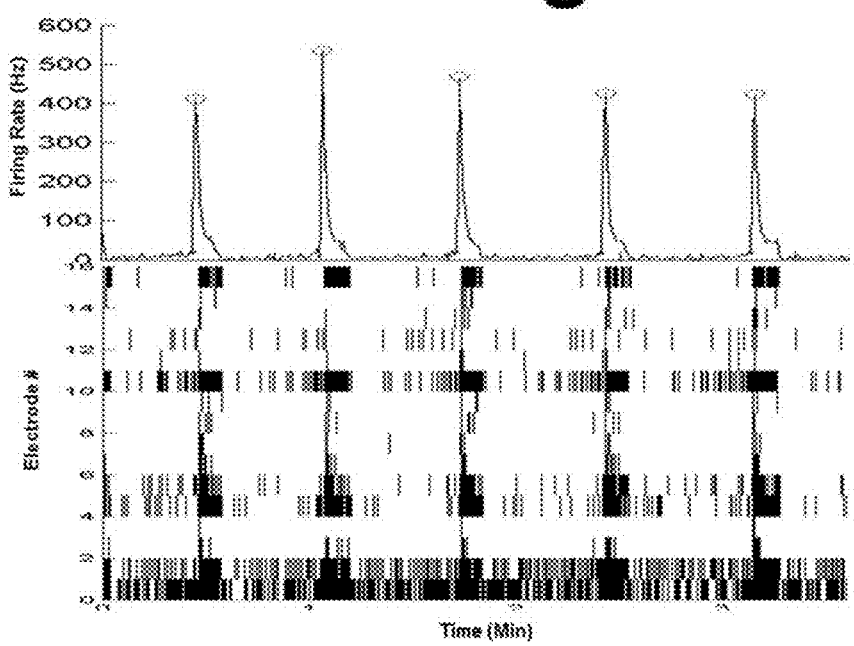

Two examples of neuronal cultures (Day 12) that express similar E/I ratios (70:30) are shown in FIG. 9. iCell® DopaNeurons (top) are midbrain neurons, while the Glutamatergic70 (bottom) cell type are cortical neurons. Note both networks displayed similar network burst intensity levels and a post-burst rumbling level, which was more pronounced in iCell® DopaNeurons.

Figure 11:
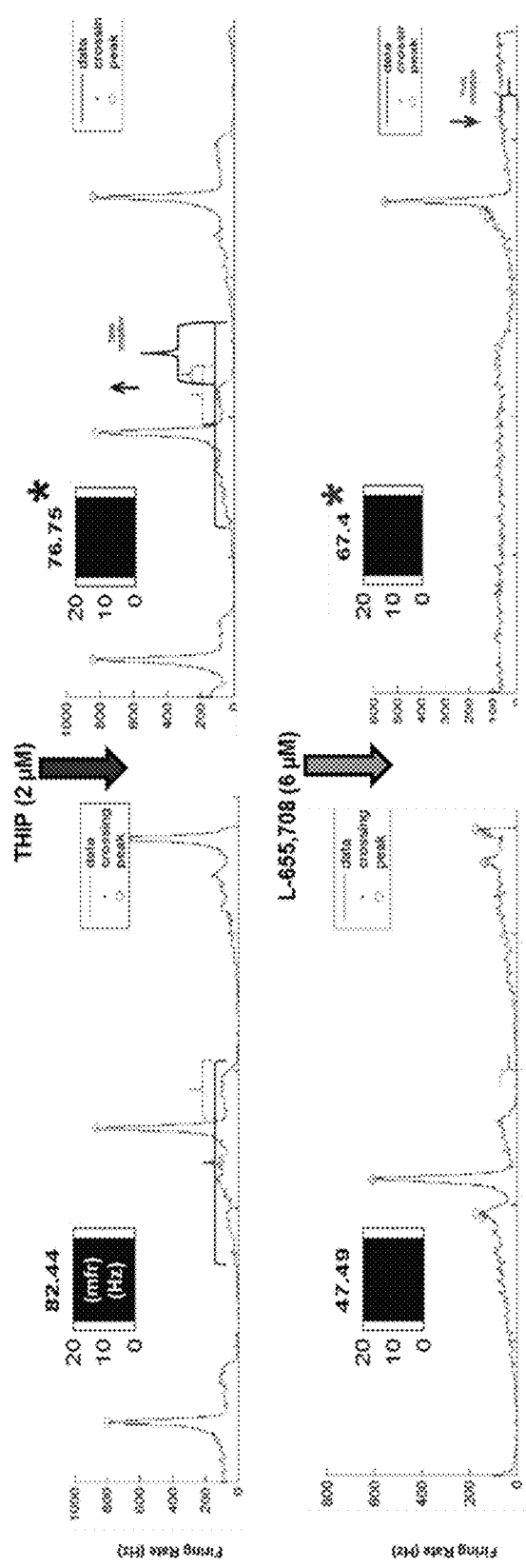
FIG. 11: Two examples of excitability pharmacology, THIP (top) and L-655,708 (bottom), on iCell® DopaNeuron cultures are shown. THIP is a sleep aid and activates tonic inhibition, while L-655,708 decreases tonic inhibition, is a cognitive enhancer and is also known to induce seizures. Tonic inhibition is an inhibitory current that helps set the resting membrane of the cell, as well as shunts excitatory potentials from depolarizing the cell towards threshold of an action potential. Results show that neither pharmacological agent altered network burst intensity, but both altered post-bursting behaviors. THIP shortened the durations of the entire burst and the post-burst rumble, and conversely, L-655,708 abolished the 'after-quiet' by inducing a continuous rumbling of activity. These experiments show that the network synchrony of the culture was appropriately responsive to known excitatory-regulating pharmacology.

Two examples of excitability pharmacology, THIP (top) and L-655,708 (bottom), on iCell® DopaNeuron cultures are shown in FIG. 11. THIP activates tonic inhibition, while L-655,708 decreases tonic inhibition. Neither pharmacological agent altered network burst intensity, but both altered post-bursting behaviors. THIP shortened the time of the entire burst, as well as the post-burst rumbling time. Conversely, L-655,708 abolished the 'after-quiet' and de-synchronized the network, inducing a continuous rumble of activity that dominated activity.

Figure 12:
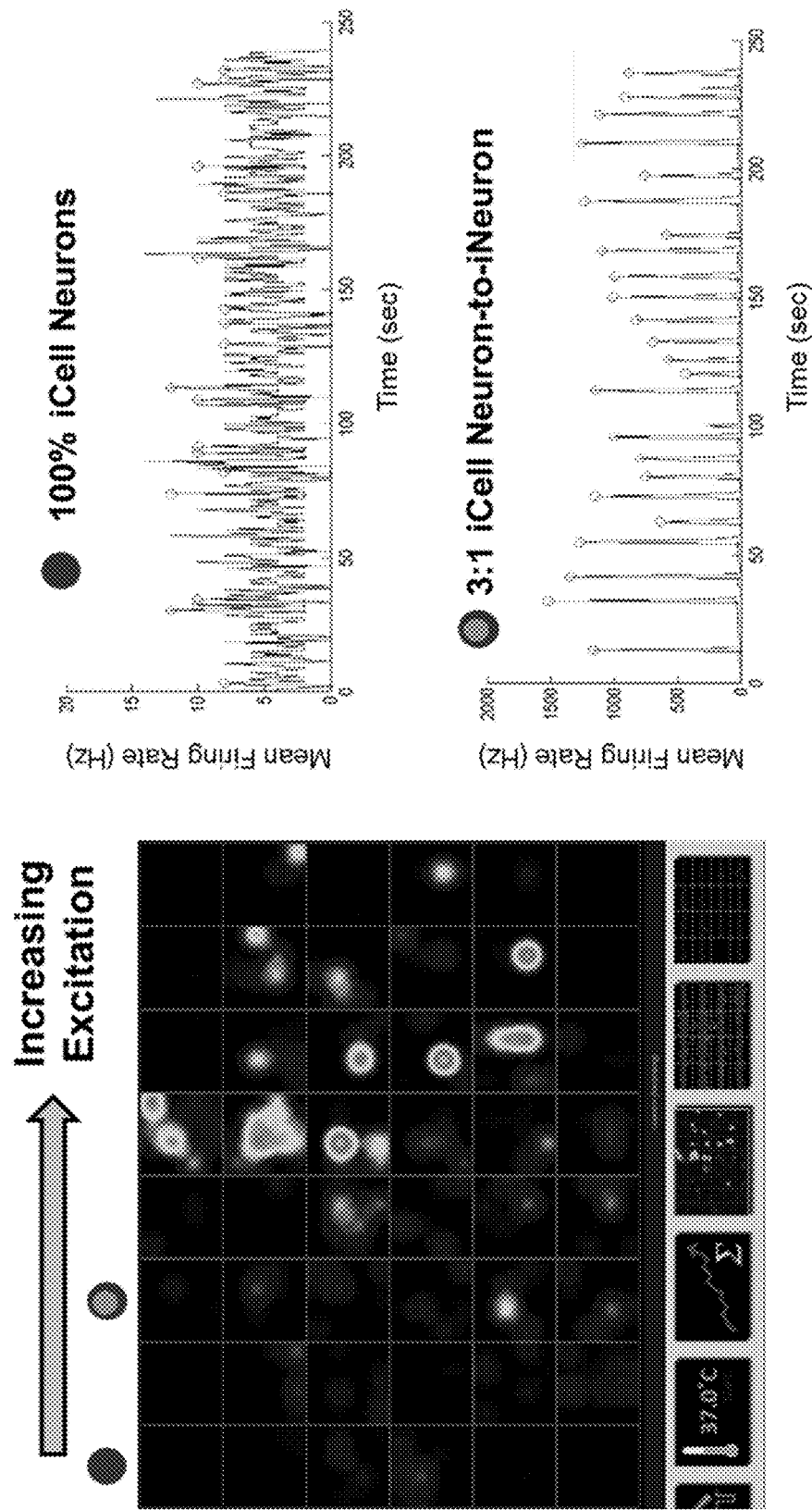
FIG. 12: Bursting observed with neuronal cultures derived from human iPS cells.
Figure 13:
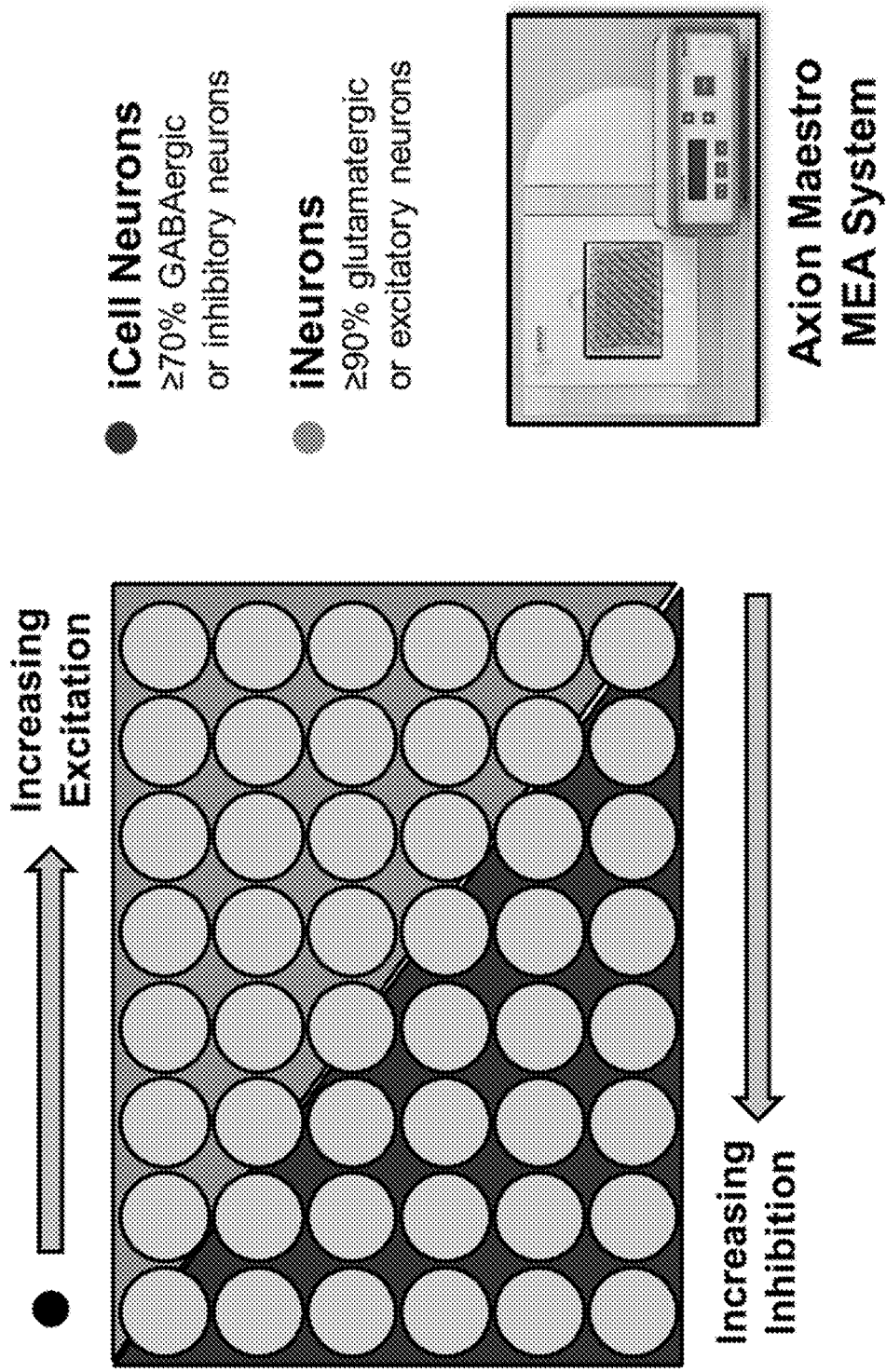
FIG. 13: Differing ratios of excitatory and inhibitory neurons may be co-cultured in a single MEA.

Synchronous bursting was observed in cultured neurons. Simultaneous firing across the majority of all 16 electrodes within the same MEA well was observed. These intense burst of spikes indicate neuronal networks have formed and cells are firing together synchronously. As shown in FIG. 12, a bursting phenotype was observed with human iPS cell-derived neuronal cultures; in particular, notice the scale of each y-axis in FIG. 11. As shown in FIG. 13, differing ratios of excitatory and inhibitory neurons may be co-cultured in a multi-electrode array such as, e.g., MEA.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

PCT/US2011/046796
U.S. patent application Ser. No. 14/664,245
U.S. Pat. Pub. 2002/0168766
U.S. Pat. Pub. 2003/0022367
U.S. Pat. Pub. 2003/0211603
U.S. Pat. Pub. 2007/0238170
U.S. Pat. Pub. 2008/0171385
U.S. Pat. Pub. 2009/0029462
U.S. Pat. Pub. 2011/0104125
U.S. Patent Pub. 2012/0276063
U.S. Pat. No. 7,820,439
U.S. Pat. No. 8,153,428
U.S. Pat. No. 8,252,586
U.S. Pat. No. 8,426,200
U.S. Pat. No. 8,513,017
U.S. Pat. No. 8,546,140
U.S. Pat. No. 8,735,149
U.S. Pat. No. 8,741,648
U.S. Pat. No. 8,796,022
WO2011130675
WO2012080248
WO2013067362
WO2013163228
WO2014172580
WO 2011091048,
Allen et al. "Astrocyte glypicans 4 and 6 promote formation of excitatory synapses via GluA1 AMPA receptors" *Nature* 486, 410-414, 2010.
Bardy et al., "Neuronal medium that supports basic synaptic functions and activity of human neurons in vitro. *Proc Natl Acad Sci USA.* 2015 Apr. 13. pii: 201504393, 2015.
Chen et al., *Cell,* 133:1106-1117, 2008.
Chen et al., *Nature Methods* 8:424-429, 2011.
Dani et al., "Reduced cortical activity due to a shift in the balance between excitation and inhibition in a mouse model of Rett syndrome," *Proc. Nati. Acad.* 2005.
Gibson et al., "Imbalance of neocortical excitation and inhibition and altered UP states reflect network hyperexcitability in the mousemodel of fragile X syndrome," *J. Neurophysiol* 100: 2615-2626, 2008.
Hagerman and Hagerman, "The fragile X premutation: into the phenotypic fold," *Curr. Opin. Genet. Dev.* 12: 278-283, 2002.
Ludwig et al., *Nat. Biotechnol.,* 24 (2):185-187, 2006b.
Ludwig et al., *Nat. Methods,* 3 (8):637-46, 2006a.
Massimini et al., "Cortical mechanisms of loss of consciousness: insight from TMS/EEG studies," *Arch Ital Biol* 150 (2-3):44-55, 2012.
Schwartz et al., Methods 45 (2): 142-158, 2008.
Tabuchi et al., "A neuroligin-3 mutation implicated in autism increases inhibitory synaptic transmission in mice," *Science* 318, 71-76, 2007.
Takahashi and Yamanaka, *Cell,* 126:663-676, 2006.
Takahashi et al., *Cell,* 126 (4):663-76, 2007.
Takahashi et al., *Cell,* 131:861-872, 2007.
Yu et al., *Science,* 318:1917-1920, 2007.
Yu and Thomson, *Genes Dev.* 22 (15):1987-97, 2008.
Yu et al., *Science,* 324 (5928):797-801, 2009.
Zhang and Sun, "The balance between excitation and inhibition and functional sensory processing in the somatosensory cortex," *Int Rev Neurobiol* 97:305-33, 2011.
Zhang et al., *Neuron,* 78:785-798, 2013.

What is claimed is:

1. An in vitro method for producing a cell culture comprising a population of neurons, wherein the method comprises;
   (a) combining or mixing a plurality of excitatory neurons and inhibitory neurons in vitro at a ratio of higher proportion of excitatory neurons compared to inhibitory neurons, and
   b) culturing the neurons for a period of lime sufficient to allow for the formation of a neural network; wherein both the excitatory neurons and the inhibitory neurons are obtained from human induced pluripotent stem (iPS) cells; wherein the ratio of excitatory neurons to inhibitory neurons is sufficient to allow for the generation of synchronous neuron firing or synchronous action potentials by the neural network; wherein the population of neurons comprises from about 40% to about 90% excitatory neurons and from about 60% to about 10% inhibitory neurons; wherein the excitatory neurons form glutarnatergic synapses and express vGLUT1; and wherein the inhibitory neurons form GABA synapses and express vGAT and GAD67.

2. The method of claim 1, wherein the culture of neurons comprises astrocytes, wherein the astrocytes are obtained from pluripotent stem cells.

3. The method of claim 1, wherein the iPS cells are obtained from a healthy donor.

4. The method of claim 1, wherein the iPS cells are obtained from a subject with a disease.

5. The method of claim 4, wherein the disease is a neurological or neurodegenerative disease.

6. The method of claim 5, wherein the disease is autism, epilepsy, schizophrenia, ADHD, ALS, or a bipolar disorder.

7. The method of claim 1, wherein the population of neurons comprises from about 45% to about 80% excitatory neurons and from about 55% to about 20% inhibitory neurons.

8. The method of claims 7, wherein from about 5% to about 25% of the cells in the cell culture are astrocytes, wherein the astrocytes are obtained from iPS cells.

9. The method of claim 8, wherein the astrocytes are obtained from human iPS cells.

10. The method of claim 1, wherein the population of neurons is cultured on a multi-electrode array.

11. The method of claim 10, wherein the multi-electrode array is a Maestro MEA.

12. The method of claim 10, wherein the multi-electrode array comprises at least 8 electrodes.

13. The method of claim 10, wherein the multi-electrode array comprises at least 16 electrodes.

14. The method of claim 10, wherein the multi-electrode array comprises a plurality of cultures of said neurons in distinct wells in the multi-electrode array, wherein the ratios of excitatory to inhibitory neurons varies between the cultures.

15. The method of claim 1, wherein the method further comprises contacting the population of neurons with a test compound.

16. The method of claim 15, wherein the test compound can modulate neurotransmission.

17. The method of claim 1, further comprising detecting or measuring the electrical or neuronal activity of the population.

18. The method of claim 17, wherein said detecting or measuring comprises measuring the voltage produced by said population.

19. The method of claim 18, wherein neuronal electrical activity data from said detecting or measuring is analyzed, and wherein the population of neurons is cultured on a multi-electrode array.

20. The method of claim 1, wherein the population of neurons is cultured on a multi-electrode array, and wherein the synchronicity is detected in a plurality of electrodes on the multi-electrode array.

21. The method of claim 7, wherein the population of neurons comprises from about 45% to about 55% excitatory neurons and from about 55% to about 45% inhibitory neurons.

22. The method of claim 2, wherein from about 10% to about 55% of cells in the cell culture are astrocytes, wherein the astrocytes are obtained from human iPSC.

* * * * *

UNITED STATES PATENT AND TRADEMARK OFFICE
CERTIFICATE OF CORRECTION

PATENT NO. : 10,444,227 B2
APPLICATION NO. : 14/830162
DATED : October 15, 2019
INVENTOR(S) : Kile P. Mangan et al.

Page 1 of 1

It is certified that error appears in the above-identified patent and that said Letters Patent is hereby corrected as shown below:

In the Claims

In Claim 1, Column 22, Line 58, delete "lime" and insert --time-- therefor.

In Claim 1, Column 23, Line 2, delete "glutarnatergic" and insert --glutamatergic-- therefor.

Signed and Sealed this
Eleventh Day of February, 2020

Andrei Iancu
*Director of the United States Patent and Trademark Office*